(12) United States Patent
Dias et al.

(10) Patent No.: US 12,343,449 B2
(45) Date of Patent: Jul. 1, 2025

(54) OSTEOCONDUCTIVE FIBERS, MEDICAL IMPLANT COMPRISING SUCH OSTEOCONDUCTIVE FIBERS, AND METHODS OF MAKING

(71) Applicant: DSM IP Assets B.V., Heerlen (NL)

(72) Inventors: Aylvin Jorge Angelo Athanasius Dias, Echt (NL); Noel L. Davison, Echt (NL); Anne Marie Persson, Echt (NL); Ynze Mengerink, Echt (NL); Paul Mathieu De Bueger, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 1089 days.

(21) Appl. No.: 16/976,123

(22) PCT Filed: Mar. 6, 2019

(86) PCT No.: PCT/EP2019/055604
§ 371 (c)(1),
(2) Date: Aug. 27, 2020

(87) PCT Pub. No.: WO2019/170769
PCT Pub. Date: Sep. 12, 2019

(65) Prior Publication Data
US 2021/0299332 A1 Sep. 30, 2021

(30) Foreign Application Priority Data
Mar. 6, 2018 (EP) ..................... 18160350

(51) Int. Cl.
*A61L 27/46* (2006.01)
*A61L 27/54* (2006.01)
*A61L 27/56* (2006.01)
*C08L 23/06* (2006.01)
*D01F 1/10* (2006.01)
*D01F 11/06* (2006.01)

(52) U.S. Cl.
CPC ............... *A61L 27/46* (2013.01); *A61L 27/54* (2013.01); *A61L 27/56* (2013.01); *C08L 23/06* (2013.01); *D01F 1/10* (2013.01); *D01F 11/06* (2013.01); *A61L 2400/18* (2013.01); *A61L 2430/02* (2013.01); *A61L 2430/10* (2013.01); *C08L 2207/068* (2013.01)

(58) Field of Classification Search
CPC .......... A61L 27/46; A61L 27/54; A61L 27/56; A61L 2400/18; A61L 2430/02; A61L 2430/10; A61L 2430/06; A61L 31/127; A61L 31/146; A61L 31/148; A61L 17/10; A61L 27/18; A61L 31/06; A61L 31/16; C08L 23/06; C08L 2207/068; D01F 1/10; D01F 11/06; D01F 6/04; D06M 10/025; A61B 17/06166; A61B 2017/00831; A61B 2017/0406
See application file for complete search history.

(56) References Cited

U.S. PATENT DOCUMENTS

| 3,839,068 | A | 10/1974 | Miura |
| 4,024,871 | A | 5/1977 | Stephenson |
| 4,739,013 | A | 4/1988 | Pinchuk |
| 4,810,749 | A | 3/1989 | Pinchuk |
| 5,133,742 | A | 7/1992 | Pinchuk |
| 5,229,431 | A | 7/1993 | Pinchuk |
| 5,298,028 | A | 3/1994 | Hsu |

(Continued)

FOREIGN PATENT DOCUMENTS

| DE | 10055465 A1 | 11/2000 |
| JP | 6339521 A2 | 12/1994 |

(Continued)

OTHER PUBLICATIONS

Boccaccini et al. (Journal of Biomedical Materials Research Part B: Applied Biomaterials 2003 67B:618-626), (Year: 2003).*
Blaker et al. (Biomaterials 2004 25:1319-1329). (Year: 2004).*
Liming Fang, et al., Processing of hydroxyapatite reinforced ultra-high molecular weight polyethylene for biomedical applications, Biomaterials, 2005, pp. 34178-3478, 26.
Alencar De Queiroz, et al., A Novel Bone Scaffolds Based on Hyperbranched Polyglycerol Fibers Filled with Hydroxyapatite Nanoparticles: In Vitro Cell Response, Key Engineering Materials, 2008, pp. 633-636, vol. 396-398.
Liming Fang, et al., Processing and Mechanical Properties of HA/UHMWPE Nanocompsites, Biomaterials, 2006, pp. 3701-3707, vol. 27.

(Continued)

*Primary Examiner* — Snigdha Maewall
(74) *Attorney, Agent, or Firm* — Nixon & Vanderhye, P.C.

(57) ABSTRACT

The disclosure relates to high-strength polyolefin composite fibers, which fibers have a fiber body comprising a composition consisting of polyolefin; 1-30 mass % of bioceramic particles having particle size D50 of 0.01-10 μm; at most 0.05 mass % of residual spin solvent; optionally 0-3 mass % of other additives; and wherein the sum of a)-d) is 100 mass %; and which fibers have bioceramic particles exposed at their surface, and show bioactivity. The composite fibers based on a composition of polyolefin with bioceramic particles mixed therein show particles being exposed at the fiber surface by techniques like AFM and XPS, and although apparently only a relatively small amount of bioceramic particles is exposed at the fiber surface, this appears sufficient for effective interaction with their environment and stimulating a positive biological response as demonstrated by in vitro cell studies.
The present disclosure also concerns a method of making the high-strength composite fibers via a gel spinning process, fibrous articles comprising said bioactive composite fibers. Further embodiments concern use of these fibrous articles as a component of a medical implant or as a medical implant, especially as permanent high-strength orthopedic implants for repairing bone fractures or torn ligaments or tendons. Other embodiments include medical devices or implants comprising said fibrous articles.

19 Claims, 12 Drawing Sheets

(56) References Cited

U.S. PATENT DOCUMENTS

| | | | |
|---|---|---|---|
| 5,779,729 A | | 7/1998 | Severini |
| 6,296,667 B1 | | 10/2001 | Johnson et al. |
| 8,562,647 B2 | | 10/2013 | Kaiser et al. |
| 2001/0001113 A1 | | 5/2001 | Lim et al. |
| 2003/0220700 A1 | | 11/2003 | Hammer et al. |
| 2004/0228905 A1 | * | 11/2004 | Greenspan .............. A61Q 5/00 514/35 |
| 2006/0216321 A1 | | 9/2006 | Lyu et al. |
| 2010/0268331 A1 | | 10/2010 | Simmelink et al. |
| 2011/0022085 A1 | | 1/2011 | Murphy et al. |
| 2015/0018878 A1 | * | 1/2015 | Rizk ................... A61L 31/127 606/232 |
| 2016/0144066 A1 | | 5/2016 | Long et al. |
| 2016/0271296 A1 | | 9/2016 | Jongpaiboonkit et al. |
| 2016/0287242 A1 | | 10/2016 | Troxel et al. |

FOREIGN PATENT DOCUMENTS

| | | | |
|---|---|---|---|
| JP | 6339522 | | 12/1994 |
| JP | 2011506787 A | | 3/2011 |
| JP | 2014504315 A | | 2/2014 |
| JP | 2014193272 A | | 10/2014 |
| WO | 2000048552 A1 | | 8/2000 |
| WO | 2002070031 A1 | | 9/2002 |
| WO | 2003103735 A1 | | 12/2003 |
| WO | WO-2006020644 A2 * | 2/2006 | ............. A61L 27/54 |
| WO | WO2009015420 A1 | | 2/2009 |
| WO | 2014060591 A1 | | 4/2014 |
| WO | WO2017133903 A2 | | 8/2017 |

OTHER PUBLICATIONS

Wutticharoenmongkol, et al., Novel Bone Scaffolds of Electrospun Polycaprolactone Fibers filled with Nanoparticles, Journal of Nanoscience and Nanotechnology, 2006, pp. 514-522, vol. 6.

Yeong-Mu Ko, et al., O2/AR Plasma Treatment for Enhancing the Biocompatibility of Hydroxyapatite Nanopowder and Polycaprolactone Composite Film, Journal of Nanoscience and Nanotechnology, 2015, pp. 6048-6052, vol. 15.

Davison, N., In vivo performance of microstructured calcium phosphate formulated, Acta Biomaterials, 2012, 8 (2012) 2759-2769, 8 (2012, Elsevier).

Dorozhkin, S.V., Calcium orthophosphate deposits: Preparation, properties and biomedical applications, Materials Science and Engineering C, 2015, 272-326, C55.

Lin, H., Biomedical coatings on polyethylene terephthalate artificial ligament, J Biomed Mater Res Part A, 2015.

Pfeiffer, F.M., The histologic and biomechanical response of two cemmercially available small glenoid anchors for use of labral repairs, J Shoulder Elbow Surg, 2014, pp. 1156-1161, 23, Elsevier.

International Search Report, May 27, 2019.

Written Opinion of the International Searching Authority, May 27, 2019.

Aydin et al.,, Interaction of Osteoblasts with Macroporous Scaffolds Made of PLLA/PCL Blends Modified with Collagen and Hydroxyapatite;, Advanced Engineering Materials, 2009, pp. B83-B88, 11 (8).

Barnes et al, Using scratch testing to measure the adhesion strength of calcium phosphate coatings applied to poly(carbonate urethane) substrates, Journal of Mechanical Behavior of Biomedical Materials, 2012, pp. 128-138, 6.

Bretcanu, et al., Bioactivity of degradable polymer sutures coated with bioactive glass, Journal of Materials Science: Materials in Medicine, 2004, pp. 893-899, vol. 15.

Chetty et al. 2007, Hydroxyapatite-coated polyurethane for auricular cartilage replacement: An in vitro study, Journal Biomedical Materials Research Part A, 2007, pp. 475-482, (DOI 10.1002/jbm. a).

Debbabi et al.,, Simultaneous optimization of mechanical properties of braided polyethylene terephthalate suture subjected to hot-stretching treatment, Journal of Industrial Textiles, 2016, pp. 1417-1439, 45(6).

Geary et al. Mater. Sci: Mater. Med (2008) 19:3355-3363 (DOI 10.1007/s10856-008-3472-8).

Jonathan Pratten, In Vitro Attachment of *Staphylococcus epidermidis* to Surgical Sutures with an without Ag-containing Bioactive Glass Coating, Journal of Biomaterials Applications, Jul. 2004, pp. 47-57, vol. 19.

Li et al., Enhancement of the osseointegration of a polyethylene terephthalate artificial ligament graft in a bone tunnel using 58S bioglass, International Orthopaedics (SICOT), 2012, pp. 191-197, (DOI: 10.1007/s00264-011-1275-x).

Li Wancong, Extraction, degree of polymerization determination, Elsevier, Jan. 1, 2015, 1-5, NA, Elsevier, NA, CN.

Li et al., Hydroxyapatite coating enhances polyethylene terephthalate artificial ligament graft osseointegration in the bone tunnel, International Orthopaedics, 2010, pp. 1561-1567, (DOI: 10.1007/s00264-010-1158-6).

Wu Yang et al., The Effect of Bioactive Glass Modified Polyethylene Terephthalate on Bone Healing, Chinese Excellent Doctoral Dissertation Full-text Database (Master) Medical Science and Technology Series, Mar. 15, 2013, pp. 11-16, vol. 3.

Yilgor, et al., Structure-Morphology-Property Behavior of Segmented Thermoplastic Polyurethanes and Polyureas Prepared without Chain Extenders, Polymer Reviews, 2007, pp. 487-510, vol. 47.

* cited by examiner

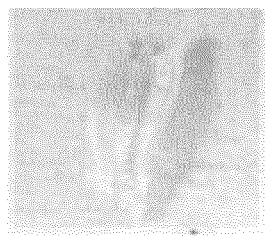 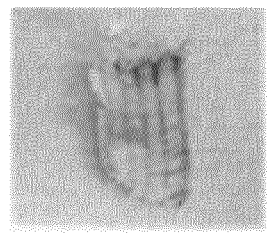 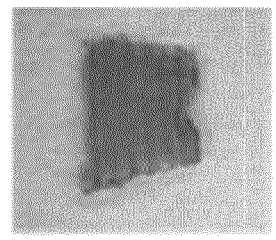
7A　　　　　　　7B　　　　　　　7C
Fig. 7

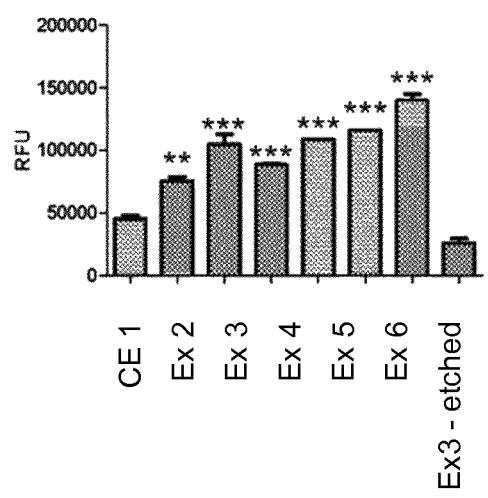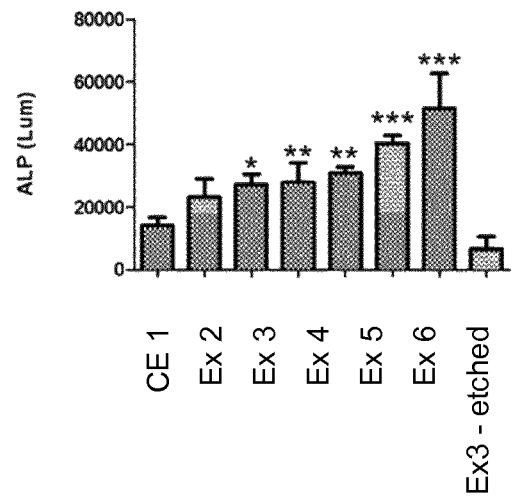
Fig. 8A                    Fig. 8B

OSTEOCONDUCTIVE FIBERS, MEDICAL IMPLANT COMPRISING SUCH OSTEOCONDUCTIVE FIBERS, AND METHODS OF MAKING

CROSS-REFERENCE TO RELATED APPLICATIONS

This application is a U.S. national phase entry under 35 USC 371 of international application PCT/EP2019/055604, filed 6 Mar. 2019, which designated the U.S. and claims priority to European Application 18160350.7, filed 6 Mar. 2018, the entire contents of each of which is hereby incorporated by reference in its entirety.

FIELD

The disclosed inventions relate to polyolefin fibers showing bioactivity, particularly osteoconductive properties, and which fibers are suitable for use in a medical implant; like high-strength ultra-high molecular weight polyethylene fibers having bioactive inorganic particles like calcium phosphates at their surface to promote bone growth on the fibers or on an article comprising such fibers after implantation. The inventions also relate to a method of making such osteoconductive fibers, and to medical implants like flexible tissue anchors, bone fixation devices, and textile-based scaffolds for bone regeneration, which implants comprise said fibers.

BACKGROUND

Fibrous articles, like braided cables or knitted and woven textile constructs made from fibers or filaments spun from synthetic polymers, have found various applications as a component of a medical device, such as in surgical sutures and cables, artificial ligaments and tendons, hernia meshes, and flexible tissue anchors.

A tissue anchor as used in orthopedic surgery is an implantable medical device that for example is applied to re-attach soft tissue like a tendon to bone or to attach an artificial tendon to bone; as in shoulder instability repair or knee ligament reconstruction, like anterior cruciate ligament (ACL) reconstruction. Attachment to bone is typically obtained by inserting an anchor into a hole drilled in the bone (also called bore or tunnel) and connecting to soft tissue via a suture that is attached to the anchor. A tissue anchor may be rigid and non-flexible, like a solid screw or plug molded from metal or biocompatible polymer. A disadvantage of these rigid anchors is that relatively large holes need to be made in the bone. Alternatively, flexible anchors, such as a fibrous article comprising fibers spun from a biocompatible polymer are applied, which anchors have the advantage that they generally require significantly smaller bone tunnels, while providing at least similar strength.

In U.S. Pat. No. 8,562,647B2 a flexible anchor is described, which comprises a fibrous body or sleeve defining a passage through which a suture construct passes and to which it is connected, at least one self-locking adjustable loop, and leg portions. After inserting into a bore in a bone, an anchoring mass is formed by changing the shape of the flexible anchor by applying tension to the adjustable loop via pulling on the ends of the connected suture. The suture construct and fibrous sleeve are typically made by braiding multiple strands of non-resorbable, biocompatible polymer fibers; like a polyester, more specifically a polyethylene terephthalate (PET) polymer or copolymer. Such fiber-based flexible tissue anchor is often referred to as a "soft anchor" or "all-suture anchor" (ASA) in the art.

WO2017/133903 discloses an implantable textile suture anchor comprising a braided collapsible member having a plurality of eyelets and at least one thread attached to it, which thread is guided through the eyelets such that by pulling on the at least one thread the member collapses and laterally expands. The member and thread are braided from strands of biocompatible fibers like ultra-high molecular weight polyethylene (UHMWPE).

UHMWPE is a synthetic polymer that shows good biocompatibility in combination with high biostability or bio-inertness, and is being used in biomedical devices, like joint prostheses for knee or hip repair surgery, for quite some time already. An unmodified olefin-based polymer like UHMWPE is known to have unfavorable surface properties for cell attachment and proliferation of osteoblasts and fibroblasts, and such polyolefin does not intrinsically bind to bone (which is also not desired for e.g. a femoral head of a hip joint). This is generally ascribed to the chemical inertness and apolar or hydrophobic character of polyolefins like polyethylenes.

Fibers made from UHMWPE, especially such fibers made via a so-called gel spinning process, generally show very high strength properties, good durability, and low friction; making them suitable non-biodegradable materials for making low profile fiber constructions for use in biomedical applications like sutures and artificial tendons and ligaments.

Orthopedic implants, like an ASA, comprising unmodified UHMWPE fibers will be prone to fibrous tissue encapsulation after implantation, because of foreign body response in the bone tunnel in which they have been implanted. Without strong bonding between host bone and implant, continuously changing loads and/or micromotion of the implant may lead to implant instability and loosening, bone tunnel widening, and cyst formation (see e.g. Pfeiffer et al., DOI: 10.1016/j.jse.2013.12.036). Such insufficient bonding hampers actual use of UHMWPE fibers in bone anchoring applications.

From a biological perspective, the ideal material for reconstructive surgery is autogenic bone or tissue, because of its biocompatibility, osteoconductivity, osteoinductivity, and non-immunogenicity. Limitations in harvesting adequate amounts of tissue or bone material and disadvantages of multiple operations, however, make the 'ideal' material far from ideal for many surgical procedures. An alternative is using allogeneic or xenogeneic bone-derived grafts, but such materials may induce disease transfer, high immunogenic response, or show unreliable degradation behavior. Therefore, synthetic implant materials or biomaterials, like metals, ceramics, polymers and composites, find increasing use in clinical applications. Several bioactive materials have been clinically applied as e.g. bone fillers and bone graft substitutes for quite some years, because they do not illicit foreign body encapsulation by the host but rather bond directly to bone due to their reactive, biomimetic surfaces. Such osteoconductive materials allow native bone tissue to bond and grow on the material surface resulting in osseointegration; i.e. mechanical anchorage of the implant in bone. Examples of such bioactive materials include calcium phosphates like hydroxyapatite (HA), beta-tricalcium phosphate (bTCP), and mixed inorganic oxides referred to as bioglass. Clinical use of these bioactive ceramics is generally confined to bone void fillers rather than load bearing bone substitutes, due to their low strength and brittleness.

Most synthetic polymers as such are not bioactive but bioinert, and therefore do not bond to bone upon implantation but instead are typically encapsulated by fibrous tissue. To overcome this shortcoming in orthopedic use, composites of polymer and bioactive materials (i.e. "biocomposites") have been shown to potentially combine the desired biological effects of the bioactive materials along with inherent advantages of polymers, including good material mechanics, the option to tailor properties by varying composition and addition of further compounds, and freedom in design, processing and shaping.

Polymer-ceramic composites as bioactive material may be made by mechanical mixing of polymer and ceramic particles, generally resulting in a polymer continuous matrix with bioactive ceramic (also called bioceramic) particles dispersed therein. Mixing may be done by processing in the melt state of the polymer, but also in solution or dispersion to allow lower processing temperature. Spinning of fibers from a composite material, however, is often hampered by the particulate loading, for example leading to instabilities and frequent breakage in the spinning process. Other disadvantages of such composites may include undesired changes in bulk properties. Incorporating ceramic particles into a polymer may for example induce polymer degradation or hamper molecular orientation and crystallization, which typically results in less mechanical strength. In addition, the particles being dispersed throughout the polymer may result in ceramic particles being fully covered by the polymer in the composite; the particles not being available for interaction with tissue or fluid after implantation.

The influence of polymer on surface exposure and osteoconductivity of bioceramic particles dispersed in a polymer matrix was studied by Davison et al. (DOI: 10.1016/j.actbio.2012.04.007). In this publication it is shown that when bioceramic particles are embedded and fully encapsulated in a polymeric matrix that requires a long time to dissolve in vitro and in vivo, the particles show no osteoconductivity in a bone defect model, but rather will be encapsulated by fibrous tissue formation. In contrast, using polymer compositions that easily dissolve or degrade promoted bone formation and bone bonding; which was explained as the bioceramic particles becoming timely exposed to the physiological environment.

For these reasons, making osteoconductive implants via surface modification of a polymer article or fiber has been extensively studied in last decades. Dorozhkin (DOI: 10.1016/j.msec.2015.05.033) reviewed in 2015 almost 1000 publications relating to methods of applying calcium phosphate ($CaPO_4$) deposits on implant materials. It was concluded that although it is generally accepted that $CaPO_4$-modification may improve osteoconduction, further studies are still needed to better understand bone responses to coated implant surfaces.

In 2015 Li et al. published a review of publications on various biomedical coatings on PET artificial ligaments (DOI: 10.1002/jbm.a.35218) and concluded that several coatings on PET, for example a coating comprising hydroxyapatite, can increase bioactivity but also show several limitations; including bioceramic particle agglomeration and poor adhesion to PET substrates. Li et al. further concluded that complete characterization of critical factors is lacking and that further study to enhance osseointegration and biomechanical properties of coated grafts is needed.

Documents JP6339521A2 and JP6339522A2 described surface modification of fibers made from a bioinert material like UHMWPE, by first applying a low-density polyethylene (LDPE) coating layer having a lower melting point than the fiber material itself, thermally softening this LDPE layer, and then spray coating with bioceramic particles. Plasma or chemical etching of the resulting surface is subsequently applied to partly remove the polymer from the coating layer wherein the particles are embedded, in order to expose the particles to their environment.

Publication US2011/0022085 describes the introduction of a biodegradable mineral layer onto suture material, preferably made of a biodegradable polymer, using a biomineralization process. In this method, the material surface is first functionalized with carboxylate anions, which serve as nucleation sites for a calcium- and phosphate-rich mineral layer during subsequent multi-day incubation in simulated body fluid (SBF), followed by exposure to a biological substance. The resulting bioactive suture material may be used as a vehicle for tissue healing and regeneration. Such mineralization process may be difficult to use on commercial scale, and the relatively thick mineral layer formed may be prone to mechanical delamination and disruption, with risk of particulate-induced inflammation.

In US 2016/0287242A1 an all-suture anchor is described, which anchor comprises a suture and a tubular sleeve that is composed of non-woven electrospun fibers. The fibers can be made from various degradable and non-degradable polymers, and may include a modifying agent, a biological agent or an antimicrobial agent. Preferably, the fibers have a diameter of 0.1-10 µm to encourage cellular attachment and tissue ingrowth, and to increase stability of the anchor in use. It is suggested that the modifying agent might include bioceramic particles to provide osteoconductivity, but such compositions or anchors are not described.

Publication US2015/0018878A1 describes compositions for making soft suture anchors comprising-preferably resorbable-polymer and up to 70 vol % of bioceramic particles with particle size (D50) of less than 100 µm. More specifically, compositions of a biodegradable polymer like poly(4-hydroxybutyrate) and b-TCP particles of size 20 µm as resorbable bioceramic are made by melt blending and extruding into fibers for making a sleeve or tape as suture anchor. Alternatively, a two-piece anchor in the form of a flexible collar with a taper that mates with a cone may be molded, through which anchor a suture is looped. Although improved osseointegration is stated to be an objective, no information on surface properties or bioactivity of any of the disclosed compositions or anchors is provided.

US2016/0144066A1 describes a method to prepare a bioactive all-suture anchor at the point of care, by dipping a fiber-based anchor in physiological fluid like blood from a patient and subsequently applying bioactive material by rolling or dipping the wetted anchor in bioceramic particles; making the bioactive device at the time of surgery. Preferably bioactive glass particles of 5-500 µm are applied. This approach to making a bioceramic coating may suffer from a high degree of variability and poor particle bonding to the anchor, because the dip coating procedure is done during surgery and distribution of applied ceramic particles on the anchor may be poor. Such variability and low bioceramic homogeneity are mentioned as draw-backs in the above-referenced review by Li et al., Furthermore, the method requires manipulation prior to or during surgery with the attendant infection risks of wet manipulation in the operating room. In addition, the bioceramic particles will be only bound to the fibrous anchor through interactions with the body fluid, likely hampering improvement in stability of the implant.

SUMMARY

Despite numerous publications on methods of making fiber-based articles showing osteoconductive properties for use in a medical implant, including the above cited documents, there still is a need for polymer fibers, such as high-strength polyolefin fibers, having a bioactive surface that allows osseointegration after implantation, while preserving mechanical properties needed to function in its intended medical application. It is an object of present disclosure to provide such fibers, medical implants comprising such fibers and methods of making such fibers.

The embodiments as described herein below and as characterized in the claims provide such polyolefin fibers having a surface that allows osseointegration after implantation.

In accordance with an embodiment of the invention, the fibers are high-strength composite fibers, which fibers
- have a fiber body comprising a composition consisting of
  - a) Polyolefin;
  - b) 1-30 mass % of bioceramic particles having particle size D50 of 0.01-10 μm;
  - c) At most 0.05 mass % of residual spin solvent; and
  - d) 0-3 mass % of other additives;
    wherein the sum of a)-d) is 100 mass %; and
- have bioceramic particles exposed at their surface and show bioactivity.

It was surprisingly found that the present composite fibers based on a composition of polyolefin with bioceramic particles mixed therein show particles being exposed at the fiber surface by techniques like Atomic Force Microscopy (AFM) and X-Ray Photoelectron Spectroscopy (XPS), also without additional surface treatments like an etching step. Although only a relatively small amount of bioceramic particles may be exposed at the fiber surface of composite fibers as directly resulting from a gel-spinning process, this amount appears to be sufficient for effective interaction with their environment and for stimulating a positive biological response as demonstrated by in vitro cell studies. The observed bioactivity is considered a positive indicator for in vivo osteoconductivity.

The present disclosure also concerns a method of making the bioactive high-strength composite fibers via a gel spinning process, more specifically it describes a method of making high-strength UHMWPE composite fibers comprising steps of
- Preparing a spin mixture comprising
  - UHMWPE having lintrinsic Viscosity (IV) between 5 and 40 dL/g;
  - bioceramic particles with particle size D50 of 0.01-10 μm when dispersed in decalin;
  - optionally other additives; and
  - a spin solvent;
- Spinning the spin mixture through a multiple orifice die plate to form solvent-containing composite fibers;
- Drawing the solvent-containing composite fibers in at least one drawing step; and
- Removing at least partly the spin solvent from the solvent-containing composite fibers before, during or after drawing the fibers to obtain high-strength UHMWPE composite fibers having bioceramic particles exposed at their surface and showing bioactivity.

In view of prior art disclosures and teachings, it was surprising to find that composite fibers result from this process that have a certain amount of bioceramic particles exposed at the fiber surface, and that such fibers show bioactivity in interaction with their environment, as indicated by in vitro cell studies, without the need of a post-treatment step like an etching step to expose bioceramic particles and to induce bioactivity by at least partly removing polymer that covers the particles.

Because these bioactive composite fibers also have high mechanical strength, they are well-suited for use in medical implants for which good bonding to bone is desired. Other embodiments of the invention thus concern fibrous articles comprising the bioactive composite fibers of present disclosure, which articles show osteoconductive properties.

Further embodiments concern the use of these fibrous articles as a component of a medical implant or as a medical implant, especially as permanent high-strength orthopedic implants for repairing bone fractures or torn ligaments or tendons. Examples thereof include use in flexible tissue anchors, cortical fixation devices like ACL loops, high-strength orthopedic sutures, cerclage cables, synthetic tendon and ligament grafts, and interspinous spacers or spinal disc prostheses. Other embodiments include medical devices or implants comprising said fibrous articles.

BRIEF DESCRIPTION OF FIGURES

FIGS. 7A-7C show photos of knitted structures made from fibers with 0 and 15 mass % of bioceramic particles after exposing to alizarin red, and effect of plasma etching.

FIGS. 8A and 8B depict schematically results of cell viability studies (Presto blue assay) and of and ALP assays after 28 days for different samples.

DETAILED DESCRIPTION OF EMBODIMENTS

Figure 1A:
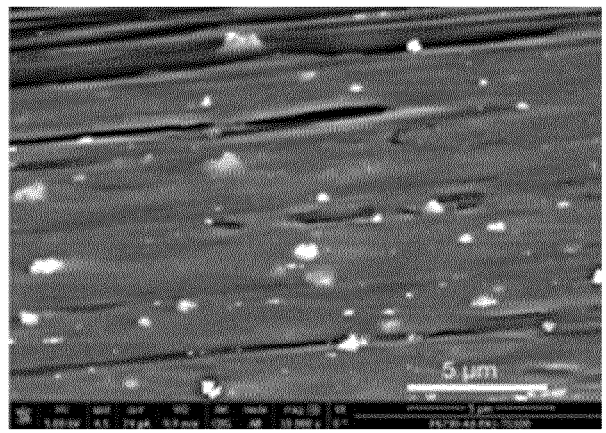
FIGS. 1A-1C show SEM micrographs for composite fibers containing 10, 15, and 20 mass % of HA.

Within the context of present disclosures, a fiber refers to an elongated body with length dimension much greater than its transverse dimensions of width and thickness. The fiber may be a long continuous thread with different cross-sectional shapes, like a ribbon, a tape, or a filament. The fiber may also have a discontinuous length, for example made by cutting continuous fibers into lengths; typically referred to in the art as staple fibers. Fibers means a plurality of one or more of such elements, like multiple filaments. A filament is understood to be a (single) thin thread with a generally round or oblong cross-section with diameter generally below 50 μm and typically made by a spinning process. A (multifilament) yarn comprises multiple filaments, like at least 5 filaments, and which filaments may be twisted. High-strength fibers have a tensile strength or tenacity of at least 15 cN/dtex as determined with a method following ASTM D885M.

A fibrous construction or fibrous article is an article comprising or substantially consisting of fibers, the article being made by interlacing at least one and generally multiple strands, wherein each strand contains at least one fiber or yarn. Examples of fibrous articles include knitted, braided, woven constructions, and non-woven constructions; like sutures, cables, tapes, textiles or fabrics for biomedical applications.

A biocompatible material or compound herein means that the substance is biologically compatible by not producing a toxic, injurious, or immunologic response when in contact with living tissue. Biodegradable means a material is susceptible to chemical degradation or decomposition into simpler components by biological means, such as by an enzymatic action. A biostable material is not biodegraded by biological means. Bioactivity is the ability of a material to elicit a specific biological response at the interface of the material and cells, body fluid or tissue, due to its (reactive) surface properties.

In case of osteoconductivity, bioactivity results in growth of bony tissue onto the surface or into the porous structure of an implant or graft. Osseointegration refers to the formation of a direct interface between an implant and bone tissue, without intervening soft tissue, and resulting in mechanical anchorage of the implant; i.e., the functional result of an osteoconductive implant. Osteogenesis is formation of bone tissue or development of bones, while osteoinduction refers to the act or process of stimulating osteogenesis.

Although this description is generally related to and illustrated with flexible tissue anchors and use thereof in tendon and ligament reconstructions, it will be understood that the composite fibers, fibrous articles and methods as disclosed herein can also be applicable to other fiber-based devices and related surgical procedures wherein osseointegration plays a role, such as for example bone fracture repair and spinal applications.

In an embodiment of the invention, high-strength composite fibers according to claim 1 are provided, which fibers are suitable for use in a medical implant. More specifically, the invention provides high-strength polyolefin composite fibers, which fibers have a fiber body comprising a composition consisting of
  a) Polyolefin;
  b) 1-30 mass % of bioceramic particles having particle size D50 of 0.01-10 µm;
  c) At most 0.05 mass % of residual spin solvent; and
  d) Optionally 0-3 mass % of other additives;
  wherein the sum of a)-d) is 100 mass %;
and which fibers have bioceramic particles exposed at their surface and show bioactivity.

In embodiments, the high-strength polyolefin fibers have a fiber body that comprises a polyolefin as its main constituent. Suitable polyolefin polymers for such fibers are polyethylene and polypropylene polymers and copolymers. Preferably the composition comprises as polyolefin one or more of a polyethylene or a polypropylene, which are essentially linear polymers comprising at most 5 mole % of comonomers, and optionally have a high molar mass; to result in fibers having high crystallinity and good mechanical properties.

In further embodiments, the high-strength polyolefin fibers have a fiber body based on a composition of ultra-high molecular weight polyethylene (UHMWPE) as polyolefin. Such fibers made from a UHMWPE composition are typically produced via a so-called gel-spinning process as described herein later, because the very high viscosity of such polymers severely hampers making fibers via for example a melt-spinning route. UHMWPE is herein understood to be a polyethylene having an intrinsic viscosity (IV) as measured on solution in decalin at 135° C., of at least 5 dL/g, like between 5 and 40 dL/g. Intrinsic viscosity is a measure for molar mass (also still commonly referred to as molecular weight, and used herein interchangeably with molar mass) that can more easily be determined than actual molar mass parameters like Mn and Mw. There are various empirical relations between IV and Mw, such relations typically being dependent on factors like molar mass distribution. Based on the equation Mw=$5.37*10^4$ [IV]$^{1.37}$ an IV of 8 dL/g would correspond to Mw of about 930 kDa, see EP0504954A1. Preferably, the IV of the UHMWPE is at least 6, 7 or 8 dL/g. Preferably, the IV is at most 30, 25, 20, 18, 16 or even at most 14 dL/g, to arrive at a balance between high mechanical properties and ease of processing. In general, the IV as measured on the UHMWPE polymer in the fiber can be somewhat lower than the IV of the polymer as used in spinning of the fibers. During a manufacturing process, like the gel-spinning method described further on, the UHMWPE may be subject to a combination of thermal, mechanical and chemical degradation, which results in chain breakage, lowering of the molar mass and/or different molar mass distribution.

In embodiments of the invention, the UHMWPE may be a linear or branched polymer, linear polyethylene being preferred. Linear polyethylene is herein understood to mean polyethylene with less than 1 side chain per 100 carbon atoms, and preferably with less than 1 side chain per 300 carbon atoms; a side chain or branch generally containing at least 10 carbon atoms. The linear polyethylene may further contain up to 5 mole % of one or more other alkenes that are copolymerisable with ethylene, e.g. C3-C12 alkenes like propene, 1-butene, 1-pentene, 4-methylpentene, 1-hexene and/or 1-octene. Side chains and comonomers in UHMWPE may suitably be measured by FTIR methods. The UHMWPE in the composition may be a single polymer grade, but also a mixture of polyethylene grades that differ in e.g. molar mass (distribution), and/or type and amount of side chains or comonomer(s).

The high-strength polyolefin composite fibers have a fiber body comprising a composition that contains 1-30 mass % of bioceramic particles. In embodiments of the invention, bioactive ceramic particles suitable for use in said composition include all inorganic materials that show the capability of direct bonding to living bone, for example by formation of biologically active bone-like apatite through chemical reaction of the particle surface with surrounding body fluid or tissue. Examples of suitable materials include various calcium salts including phosphates and so-called bioactive glasses (e.g., commercially known as Bioglass®). Barrère et al. describe in Int. J. Nanomedicine 2006: 1 (3), 317-332 various suitable types of calcium phosphates, like dicalcium phosphate anhydrate ($CaHPO_4$; DCPA), dicalcium phosphate dihydrate ($CaHPO_4 \cdot 2H_2O$; DCPD), octacalcium phosphate ($Ca_8(HPO_4)_2 \cdot 5H_2O$; OCP), tricalcium phosphate ($Ca_3(PO_4)_2$; TCP), and hydroxyapatite ($Ca_{10}(PO_4)_6(OH)_2$; HA). The ceramic particles may in addition to their main constituents comprise small or trace amounts of other (inorganic) elements or ions, like Na, Mg, Fe, Zn, Ti, Ag, Cu or —$SO_4$, or —$CO_3$, which may improve specific properties of the particles. Bioactive glass or bioglass, which is also used as a trademark, refers to mixed inorganic oxides that have a surface-reactive glass film compatible with tissues; and may be used as a surface coating in some types of medical and dental implants. The Bioglass® 45S5 grade, for example, is indicated to be a glass composed of 45 mass % $SiO_2$, 24.5 mass % CaO, 24.5 mass % Na$_2$O, and 6.0 mass % P$_2$O$_5$. The high ratio of calcium to phosphorus in this material would promote formation of apatite crystals; calcium and silica ions can act as crystallization nuclei. Glasses are non-crystalline amorphous solids that are commonly composed of silica-based materials with minor amounts of other inorganic elements. It is noted that chemical composition of inorganic compositions is typically expressed in the art as the corresponding amounts of the oxides of the inorganic elements that are present in the composition.

In other embodiments, the composition may contain mixtures of different types of bioceramic particles; like certain mixtures of HA and TCP. For example, HA is known to degrade slower in the body than TCP, and a fiber loaded with a mixture of HA and more soluble TCP may stimulate a more potent osteogenic response. The inventors hypothesized, without wishing to be bound to any theory, that a combination of such-fast resorbing and slow resorbing-bioceramic phases may be useful for both early osteogenesis and long-term osseointegration. The composition may contain mixtures of HA and TCP in 90/10 to 10/90 mass ratio, preferably HA/TCP mixtures of 85/15 to 50/50 mass ratio. In further embodiments, the composition may contain a mixture comprising an even faster resorbing bioceramic such as bioactive glasses, like HA/bioglass mixtures with 90/10 to 10/90 mass ratio, preferably such mixtures of 85/15 to 50/50 mass ratio.

In embodiments, the high-strength polyolefin composite fibers have a fiber body comprising a composition containing bioactive ceramic particles that have a particle size D50 in the range 0.01-10 μm. The particles may have various different shapes and/or cross-sections, like substantially spherical or round, elongated or oblong, or even more anisotropic shapes, such as needle-like particles. In certain embodiments, the particles applied are substantially spherical, ellipsoidal or cubical, having an aspect ratio of at most 5, 4, 3, or 2. The aspect ratio of an elongated particle is the ratio between the length along a long axis, i.e. average length (L) and the diameter of a cross-section perpendicular to the long axis, i.e. average diameter (D) of the particle, and is 1 for a spherical particle. The average diameter and the aspect ratio may be determined by using any method known in the art, for instance SEM pictures. For measuring the diameter, it is possible to make a SEM picture of the particles spread out over a surface and measuring the diameter at 100 randomly selected positions, and then calculating the arithmetic average.

Particle size and size distribution of particles can be measured with SEM or optical microscopy, or with (laser) light diffraction techniques. Within present disclosure the D50 value as measured with light diffraction according to ISO 13320:2009, e.g with a Malvern Mastersizer, on a dispersion of the bioceramic particles in decalin is defined as the particle size of the bioceramic particles. A decalin dispersion of particles can also be used in the process of making the fibers. Considering differences observed between particle size in decalin dispersion and particle size information on dry particles as provided by suppliers, it was concluded that a certain degree of (primary) particle aggregation was present in the dispersion, which aggregates may be partly broken up by shear forces during the spinning process. The particle size was not found to be specifically critical in the experiments as performed. There are indications in literature that larger particles may be more effective in interacting with body fluid and cells, but large particles may negatively affect mechanical properties of thin fibers; the fibers thus preferably contain bioceramic particles or aggregates that are smaller than 10 μm. In other embodiments, the fibers have a fiber body that contains bioceramic particles of size of at least 10, 50, 100, 200, 300, 400, or 500 nm. In further embodiments, the fiber body contains bioceramic particles having a size of at most 8, 7, 6, 5, 4, 3, 2 μm, or at most 1 μm.

The high-strength polyolefin composite fibers have a fiber body that comprises a composition containing bioceramic particles in an amount of 1-30 mass %. Although prior art suggests that a high amount of bioceramic particles will be more effective in inducing bioactivity and/or osteoconductivity for a composite material, it was now found that fibers of the invention containing relatively low amount of bioceramic particles showed noticeable bioactivity. In preferred embodiments, the composite fibers have a fiber body composition that contains at most 25, 22, 20, 18, 16, 14, 12 or even at most 10 mass %, and at least 2, 3, 4 or 5 mass % of bioceramic particles to result in fibers that show a favorable combination of bioactivity and mechanical properties like tenacity.

The high-strength polyolefin composite fibers have a fiber body comprising a composition containing at most 0.05 mass % of residual spin solvent; which spin solvent was used in a gel-spinning process for making the fibers. Gel-spinning is a specific form of solution spinning, and is typically applied for polymers that cannot, or very difficultly be melt spun into fibers. In this process a polymer solution is prepared and spun into filaments, which solution filaments solidify into a solvent-containing gel upon cooling and are then further processed; see also later. An organic solvent may also have been used during other steps of the spinning process, e.g. as an additive or spin finish. Especially for medical applications, like use of the fibers in medical implants, it is important that organic solvent or spin solvent used in making the fibers is reduced to such a level that it will not have a negative impact during use. In embodiments, the composite fibers have a fiber body composition containing less than 400, 300, 200, or 100 ppm of spin solvent, or even less than 60 ppm of residual spin solvent.

The high-strength polyolefin composite fibers have a fiber body comprising a composition that may further contain at most 3 mass %, or at most 2 or 1 mass % of other additives; like customary additives used for improving fiber spinning or fiber processing, or for affecting certain properties of the fibers. Examples of such additives include anti-static agents, anti-oxidants, stabilizers, colorants, lubricants, etc., which additives are preferably selected to be biocompatible and permitted for the targeted use of the fibers as (part of) an implant.

In other embodiments, the high-strength polyolefin composite fibers have a fiber body that comprises a composition as defined in the above, and which fiber body may optionally be provided with further components like a spin finish, which is typically applied to the fiber surface during spinning to smoothen further processing steps like drawing, winding into packages, or later converting of the fibers into fibrous articles. The fiber body may also be provided with relatively small amounts of components that have a biological or medical function, like an anti-microbial agent. Preferably, the high-strength polyolefin composite fibers have a fiber body that substantially consists of or consists of a composition as defined in the above, as any further components may increase risk of complications in medical applications like implants.

In embodiments of the invention, the composite fibers may have a cross dimension that varies widely; fibers can be typical monofilaments that can be further processed per se or can be filaments as in a multi-filament yarn. Preferably, the fibers are relatively thin threads or filaments with a fiber diameter of at most 50 μm or of at most 30, 25, 20, 15, 12, or 10 μm, and of at least 5 or 6 μm. Thin filaments may be advantageous, as they are flexible and have a relatively large surface that can come in contact and interact with body fluid and/or tissue after implantation, for example to promote osseointegration when used in a fibrous suture anchor.

In embodiments, the composite fibers are multi-filament yarns. In general, such yarns may have a widely varying linear density or titer. For practical reasons, the titer of such yarn can be from 10 to 2000 dtex. The unit dtex or decitex is typically used in fiber industry, like the related unit denier, and indicates the linear density of a strand, fiber or yarn; with 1 dtex being 1 gram per 10.000 meter of strand. The present fibers being of high-strength, low titer yarns enable making fibrous constructs like cables for use as e.g. suture or suture anchor with a relatively low profile. Preferably, the yarn has a titer of at most 1500, 1000, 800, 600, 500, 400, or 300 dtex, and at least 15, 20, or 25 dtex.

The invention also relates to methods of making the high-strength polyolefin composite fibers or yarns as defined herein. The composite fibers may be prepared by different methods as known in the art, but a particularly effective method for making bioactive composite fibers from a high molar mass polyolefin like UHMWPE proved to be a so-called gel-spinning process. In general, in a gel-spinning process a solution of the polymer in a suitable spin solvent, optionally containing dissolved and/or dispersed further components, is spun into gel fibers that are subsequently drawn before, during and/or after partially or substantially removing the spin solvent. Gel spinning of a solution of UHMWPE is well known to the skilled person; and is described in numerous publications, including EP0205960A, EP0213208 A1, U.S. Pat. No. 4,413,110, GB2042414 A, EP0200547B1, EP 0472114 B1, WO2001/73173 A1, WO2015/066401A1, in Advanced Fiber Spinning Technology, Ed. T. Nakajima, Woodhead Publ. Ltd (1994), ISBN 1-855-73182-7, and in references cited therein. All these publications are incorporated herein by reference concerning gel spinning methods for UHMWPE.

In an embodiment of the present invention, high-strength polyolefin composite fibers, especially the high-strength UHMWPE composite fibers as described herein above, are made with a gel-spinning process comprising steps of Preparing a spin mixture comprising
  a) UHMWPE having IV of between 5 and 40 dL/g, and optionally as further defined above for the composite fibers;
  b) bioceramic particles with particle size D50 of 0.01-10 μm when dispersed in decalin, and optionally as further defined above for the composite fibers;
  c) a spin solvent; and
  d) optionally other additives, as further defined above for the composite fibers;
Spinning the spin mixture through a multiple orifice die plate to form solvent-containing composite fibers;
Drawing the solvent-containing composite fibers in at least one drawing step; and
Removing at least partly the spin solvent from the solvent-containing composite fibers before, during or after drawing the fibers to obtain the high-strength UHMWPE composite fibers.

Selections of suitable UHMWPE, bioceramic particles and optionally other additives are preferably made according to the various embodiments as described herein above for the respective components. Suitable spin solvents can dissolve the polyolefin like UHMWPE at elevated temperature, whereas such solution made forms a semi-solid gel upon cooling. Examples of suitable spin solvents include aliphatic and alicyclic hydrocarbons such as octane, nonane, decane and paraffins, including isomers thereof; petroleum fractions; mineral oil; kerosene; aromatic hydrocarbons such as toluene, xylene, and naphthalene, including hydrogenated derivatives thereof such as decalin and tetralin; halogenated hydrocarbons such as monochlorobenzene; and cycloalkanes or cycloalkenes such as careen, fluorine, camphene, menthane, dipentene, naphthalene, acenaphtalene, methylcyclopentandien, tricyclodecane, 1,2,4,5-tetramethyl-1,4-cyclohexadiene, fluorenone, naphtindane, tetramethyl-p-benzodiquinone, ethylfuorene, fluoranthene and naphthenone. Combinations of said solvents may also be used as spin solvent for gel spinning of UHMWPE. For making composite fibers suitable for medical applications it was found advantageous to use relatively volatile spin solvents, like decalin or tetralin. In a preferred embodiment the spin solvent of choice is decalin. Spin solvent can be removed by evaporation, by extraction, or by a combination of evaporation and extraction routes. In preferred embodiments spin solvent is removed to a residual level of at most 500, 400, 300, 200, 100 or 60 ppm.

In an embodiment, the spin mixture is prepared by mixing the components with spin solvent using equipment like a high-speed mixer at ambient temperature, to make a dispersion of at least UHMWPE and bioceramic particles in spin solvent. In another embodiment the polyethylene is dissolved at this stage in the spin mixture by using a higher temperature.

In embodiments, standard spinning and drawing equipment may be used as is known in the art, for example a twin-screw extruder is used for the spinning step. Typically, the spin mixture is homogenized and polyethylene is dissolved in the spin solvent in the extruder operated for example in a range of 150-300° C., and then spun through the orifices into an air gap, the fibers formed are then cooled in a quench bath to solidify into gel fibers, and drawn (also called stretched) before, during or after removing at least a part of the spin solvent. Drawing or stretching steps can be performed on suitable drawing units as known in the art. To increase tensile strength and modulus of the fibers, drawing may be carried out in multiple, preferably uniaxially drawing steps, at increasing temperatures. Suitable drawing temperature is dependent on the polyolefin used, and also on residual spin solvent content of the fiber and draw ratio already applied; that is on the actual melting temperature of the (solvent-containing) fibers at each stage of the process. A first drawing step may for example comprise drawing to a draw ratio (also called stretch factor) of at least 1.5, preferably at least 3.0. Multiple drawing steps for a UHMWPE fiber may typically result in a total draw ratio of up to 10 for drawing temperatures up to 120° C., a total draw ratio of up to 25 for drawing temperatures up to 140° C., and a total draw ratio of 50 or above for drawing temperatures up to and above 150° C. in the final stage of drawing. This results in composite fibers, or multi-filament yarns consisting of composite fibers or filaments, having tenacities of at least 15.0 cN at low spin solvent content.

In alternative embodiments of the method, the bioceramic particles are added by feeding as dry powder or dispersion in spin solvent to the extruder processing the UHMWPE and spin solvent; dispersing the particles in the polymer being dissolved instead of first making a mixture of polyethylene, spin solvent and particles.

The composite fibers as obtained with this gel-spinning process surprisingly have bioceramic particles exposed at the surface and show bioactivity, as is concluded from several surface measurements and in vitro experiments using human mesenchymal stem cells (hMSCs, also simply called 'stem cells'), without needing an additional treatment to make bioceramic particles contained in a fiber body accessible or exposed at the surface.

In other embodiments, the method of the invention comprises a further step of post-treating the surface of the fibers, to at least partly remove a polyolefin layer from the fiber surface and from bioceramic particles present in such polymer surface layer of the fiber body; this way increasing the amount of bioceramic particles exposed at the surface and therewith the level of bioactivity of the composite fibers. Examples of a post-treatment step include contacting the surface of fibers with a solvent for the polyolefin, and plasma etching the surface of fibers for example in an oxygen-containing atmosphere.

In further embodiments, multi-filament yarns are provided, which yarns comprise composite fibers of present inventions and up to 50 mass % of other fibers, including fibers with lower amounts of bioceramic particles or without such bioceramic particles. Such other fibers are preferably based on biocompatible polymers, which can be biostable or biodegradable. The yarn may comprise at most 40, 30, 20 or 10 mass % of other fibers. In another embodiment the multi-filament yarn substantially consists of the composite fibers of present inventions.

In embodiments, the high-strength polyolefin composite fibers have a tensile strength or tenacity of at least 15, 20, 25, 28, 30, or even at least 32 cN/dtex. It is noted that tensile properties appear to be affected by the amount of bioceramic particles present in the fiber composition. It has been observed in the art that inorganic particles generally not contribute to strength, but often lower strength properties of a composite fiber. Indeed, some reduction in tenacity is observed for the UHMWPE composite fibers upon addition of bioceramic particles to the composition, also when corrected for reduced polyethylene content in the fibers; but strength values are still well above those of fibers commonly used for medical implants, like polyethylene terephthalate (or polyester) fibers. The tensile strength of the composite fibers may be generally lower than that of unmodified fibers; and will be typically at most about 45 cN/dtex, or at most 40, 37 or 34 cN/dtex. The composite fibers also have a high tensile modulus, typically of at least 600 cN/dtex as measured with a method following ASTM D885M. In further embodiments the composite fibers have a tensile modulus of at least 800, 900, or 1000 cN/dtex (and up to about 2000 cN/dtex).

The composite fibers of the invention have bioceramic particles exposed at their surface, as is concluded from several experiments wherein surface analyses were performed using techniques like SEM, AFM and XPS. These techniques enable characterization of a small surface area, which area can be part of the surface of a single fiber or filament; and can thus be applied on fibers, yarns, as well as on different fibrous constructions comprising the fibers or yarns.

In orienting tests, an increase in coefficient of friction of UHMWPE composite fibers upon addition of bioceramic particles has been observed, which indicates a change in surface regularity or roughness and suggests presence of particles in a surface layer and/or at the surface of the composite fibers. Change in surface properties of the composite fibers has also been demonstrated by comparative knot slippage tests, wherein braids made from UHMWPE composite fibers showed 2-3 times higher knot pull-out strength than braids made from neat UHMWPE fibers. This would be advantageous for use of the composite fibers in sutures and the like.

Surface investigation of the composite fibers with SEM techniques indicated presence of the inorganic particles in a surface layer of a fiber. SEM techniques typically may have a penetration depth on the order of 1 μm, which means that a SEM micrograph not only shows the actual surface but rather represents compositional aspects of a surface layer with thickness of up to about 1 μm. Still micrographs made on composite fibers using different acceleration voltages to vary penetration depth suggested presence of exposed bioceramic particles; that is presence of particles being partly embedded in the polymer surface and not fully covered by a layer of polymer in addition to fully embedded particles. Elemental information obtained by SEM-EDX (scanning electron microscopy combined with energy-dispersive X-ray spectroscopy) confirmed presence of inorganics.

Surface characteristics of composite fibers based on UHMWPE were further investigated with atomic force microscopy (AFM) and X-ray photoelectron spectroscopy (XPS) techniques, which allow performing (semi-) quantitative measurements on actual surfaces with low penetration depth. XPS analyses, for example, measures the elemental composition in the first 5-10 nm depth of the material surface layer, whereas AFM nicely distinguishes between hard (ceramics) and soft (organic polymer) in the material on the true surface with high spatial resolution. These techniques allow a clear distinction between inorganic particles and organic polymer, and their (relative) presence at the surface. Composite fibers of the invention, specifically UHMWPE-based composite fibers, or a fibrous structure substantially consisting of said composite fibers have a fiber surface with a surface coverage by exposed bioceramic particles of 0.1-35 area % as determined with XPS analysis and normalized to a HA surface; or have a surface with a surface coverage by exposed bioceramic particles of 0.1-35 area % as determined with AFM surface analysis. Typically, for composite fibers as directly obtained by a gel-spinning process and comprising up to 20 mass % of HA said surface coverage was found to be in the range of 0.5-6 area %. After applying a plasma etching step as post-treatment to at least partly remove a surface layer of polymer and to increase the amount of exposed bioceramic particles, said surface coverage was found to increase to about 17 area % for a composite fiber containing about 15 mass % of HA. Such plasma etched composite fibers were also found to show higher bioactivity in in vitro cell studies than the non-etched fibers. In further embodiments, the composite fibers have a fiber surface with a surface coverage by exposed bioceramic particles of at least 0.2, 0.5, or 1 area %, and at most 30, 25, 20, 15, 10 or 8 area %.

The composite fibers of the invention have bioceramic particles exposed at their surface and demonstrate bioactivity, as is concluded from multiple in vitro experiments using human mesenchymal stem cells (hMSCs, also simply called 'stem cells'). Bioceramic loading in the fibers with as little as 10 mass % HA particles (and no post-treatment) was shown to significantly increase hMSC viability versus the unloaded (neat) control fibers, e.g. after 28 days. Similarly, bioceramic-loaded fiber with 10 mass % HA was shown to significantly increase ALP activity versus the control fibers at 28 days. Additionally, increased matrix formation and biomineralization-precipitation of crystalline nodules in physiologic conditions—in both the cell matrix as well as on the fibers were observed by SEM-EDX on the bioceramic-loaded fiber samples, to an extent visibly greater than for the unloaded control. Based on these results, the composite fibers of present invention were shown to be bioactive even at the lowest bioceramic loading tested, and without an additional treatment step like surface etching. In embodiments of present disclosure, the composite fibers of the invention have bioceramic particles exposed at their surface and show at least 25% higher ALP activity after 28 days in an ALP assay than corresponding fibers containing no bioceramic particles. In further embodiments, the composite fibers show at least 30, 40, 50, 60, 70, 80, 90, 100, 150 or even 200% higher ALP activity after 28 days in an ALP assay than fibers containing no bioceramic particles, e.g. depending on amount of bioceramic particles contained in the fiber and optionally post-treatment having been applied.

The bioactive composite fibers also having high mechanical strength as disclosed herein, and fibrous articles made therewith are therefore well suited for use in medical implants for which good bonding to bone is desired, as such fibrous articles will similarly show the properties as described for the composite fibers herein. Further embodiments thus concern fibrous articles comprising the composite fibers of present disclosure and showing bioactive or osteoconductive properties. The fibrous article may substantially consist of the composite fibers of present disclosure, but the article may also comprise other biocompatible fibers that do not show similar bioactivity or other biocompatible materials. Preferably, at least those parts of a fibrous article that should show bonding to (bony) tissue when used as a medical implant contain at least 50, 60, 70, 80 or 90 mass % of the bioactive composite fibers of present disclosure.

Further embodiments concern the use of these fibrous articles as a biomedical implant or as a component of a biomedical implant, especially permanent high-strength orthopedic implants for repairing bone fractures or torn ligaments or tendons. Examples thereof include use in flexible tissue anchors, cortical fixation devices like ACL loops, high-strength orthopedic sutures, transosseos cerclage cables, synthetic tendon and ligament grafts, interspinous spacers or spinal disc prostheses, spinal fusion devices, and synthetic scaffolds to repair bone voids. A flexible tissue anchor is a device for anchoring a suture to a bone and can be applied to attach or secure soft tissue to a bone, to attach or secure bone to bone, or to attach or secure bone to structures. Non-limiting examples of soft tissue include tendons, ligaments, fascia, skin, fibrous tissues, synovial membranes, fat, muscles, nerves, and blood vessels.

Other embodiments of the invention concern biomedical devices or implants comprising the composite fibers of present disclosure or said fibrous articles comprising the composite fibers of present disclosure.

The invention is further defined by the set of exemplary embodiments as listed hereafter. Any one of the embodiments, aspects and preferred features or ranges as disclosed in this application and relating to composite fibers, fibrous articles comprising such fibers, medical devices comprising said fibers or fibrous articles, or methods of making said fibers or fibrous articles may be combined in any combination, unless otherwise stated herein or if technically clearly not feasible to a skilled person. The experiments and samples described herein below further elucidate embodiments of the invention but should not be construed as in any way limiting the scope of the claims.

[1] High-strength composite fibers suitable for use in a medical implant, which fibers have a fiber body comprising a composition consisting of a) Polyolefin;
b) 1-30 mass % of bioceramic particles having particle size D50 of 0.01-10 µm;
c) At most 0.05 mass % of residual spin solvent; and
d) Optionally 0-3 mass % of other additives;
wherein the sum of a)-d) is 100 mass %; and which fibers have bioceramic particles exposed at their surface and show bioactivity.

[2] The high-strength polyolefin fibers of embodiment [1], wherein the polyolefin is a polyethylene or polypropylene polymer or copolymer, preferably the polyolefin is an essentially linear polymer comprising at most 5 mole % of comonomers, and is of high molar mass.

[3] The high-strength polyolefin fibers of embodiment [1] or [2], wherein the high-strength polyolefin fibers have a fiber body based on a composition of ultra-high molecular weight polyethylene (UHMWPE) as polyolefin, the UHMWPE having an intrinsic viscosity (IV) as measured on solution in decalin at 135° C., of at least 5 dL/g, like between 5 and 40 dL/g, preferably IV at least 6, 7 or 8 dL/g and at most 30, 25, 20, 18, 16 or 14 dL/g.

[4] The high-strength polyolefin fibers of any one of embodiments [1]-[3], wherein the polyethylene further contains up to 5 mole % of one or more other alkenes that are copolymerisable with ethylene, preferably a C3-C12 alkene like propene, 1-butene, 1-pentene, 4-methylpentene, 1-hexene and/or 1-octene.

[5] The high-strength polyolefin fibers of any one of embodiments [1]-[4], wherein the UHMWPE in the composition is a single polymer grade, or a mixture of polyethylene grades that differ in molar mass (distribution), and/or type and amount of side chains or comonomer(s).

[6] The high-strength polyolefin fibers of any one of embodiments [1]-[5], wherein the bioactive ceramic particles are selected from so-called bioactive glasses and calcium salts like dicalcium phosphate anhydrate, dicalcium phosphate dihydrate, octacalcium phosphate, tricalcium phosphate, or hydroxyapatite.

[7] The high-strength polyolefin fibers of any one of embodiments [1]-[6], wherein the ceramic particles in addition to their main constituents comprise small or trace amounts of other (inorganic) elements or ions, like Na, Mg, Fe, Zn, Ti, Ag, Cu or —$SO_4$, or —$CO_3$.

[8] The high-strength polyolefin fibers of any one of embodiments [1]-[7], wherein the composition contains mixtures of different types of bioceramic particles, like mixtures of fast resorbing and slow resorbing particles; or mixtures of HA and TCP in 90/10 to 10/90 mass ratio, preferably HA/TCP mixtures of 85/15 to 50/50 mass ratio.

[9] The high-strength polyolefin fibers of any one of embodiments [1]-[8], wherein the composition contains a 90/10 to 10/90 mass ratio HA/bioglass mixture, preferably such mixture of 85/15 to 50/50 mass ratio.

[10] The high-strength polyolefin fibers of any one of embodiments [1]-[9], wherein the composition contains bioceramic particles that are substantially spherical or round, elongated or oblong, or anisotropic needle-like particles.

[11] The high-strength polyolefin fibers of any one of embodiments [1]-[10], wherein the bioceramic particles are substantially spherical, ellipsoidal or cubical, and have an aspect ratio of at most 5, 4, 3, or 2.

[12] The high-strength polyolefin fibers of any one of embodiments [1]-[11], wherein the composite fibers contain bioceramic particles or aggregates thereof having a size of at least 10, 50, 100, 200, 300, 400, or 500 nm, and of at most 8, 7, 6, 5, 4, 3, 2 µm, or at most 1 µm.

[13] The high-strength polyolefin fibers of any one of embodiments [1]-[12], wherein the composite fibers have a fiber body composition that contains at most 25, 22, 20, 18, 16, 14, 12 or 10 mass %, and at least 2, 3, 4 or 5 mass % of bioceramic particles.
[14] The high-strength polyolefin fibers of any one of embodiments [1]-[13], wherein the composite fibers have a fiber body composition containing less than 400, 300, 200, 100 or 60 ppm of residual spin solvent.
[15] The high-strength polyolefin fibers of any one of embodiments [1]-[14], wherein the composite fibers have a fiber body composition comprising at most 2 or 1 mass % of other additives like anti-static agents, anti-oxidants, stabilizers, colorants, or lubricants.
[16] The high-strength polyolefin fibers of any one of embodiments [1]-[15], wherein the composite fibers have a fiber body composition that further comprises a component having a biological or medical function, like an anti-microbial agent.
[17] The high-strength polyolefin fibers of any one of embodiments [1]-[16], wherein the composite fibers have a fiber body that substantially consists of or consists of a composition as defined in anyone of embodiments [1]-[16].
[18] The high-strength polyolefin fibers of any one of embodiments [1]-[17], wherein the composite fibers are monofilaments that can be further processed as such or are monofilaments that are combined in a multi-filament yarn for further use.
[19] The high-strength polyolefin fibers of any one of embodiments [1]-[18], wherein the composite fibers have a diameter of at most 50, 30, 25, 20, 15, 12, or 10 μm, and of at least 5 or 6 μm.
[20] The high-strength polyolefin fibers of any one of embodiments [1]-[19], wherein the composite fibers form a multi-filament yarn with a titer from 10 to 2000 dtex, preferably the yarn has a titer of at most 1500, 1000, 800, 600, 500, 400, or 300 dtex, and of at least 15, 20, or 25 dtex.
[21] A method of making high-strength polyolefin composite fibers or yarn as defined in any one of embodiments [1]-[20], wherein a solution of a high molar mass polyolefin in a suitable spin solvent, optionally containing dissolved and/or dispersed further components, is spun into gel fibers that are subsequently drawn before, during and/or after partially or substantially removing the spin solvent.
[22] The method of embodiment [21], wherein high-strength UHMWPE composite fibers are made with a gel-spinning process comprising steps of:
 Preparing a spin mixture comprising
  a) UHMWPE having IV of between 5 and 40 dL/g;
  b) bioceramic particles with particle size D50 of 0.01-10 μm when dispersed in decalin;
  c) a spin solvent; and
  d) optionally other additives;
 Spinning the spin mixture through a multiple orifice die plate to form solvent-containing composite fibers;
 Drawing the solvent-containing composite fibers in at least one drawing step; and
 Removing at least partly the spin solvent from the solvent-containing composite fibers before, during or after drawing the fibers to obtain the high-strength UHMWPE composite fibers.
[23] The method of embodiment or [22], wherein the spin solvent is at least one component selected from aliphatic and alicyclic hydrocarbons such as octane, nonane, decane and paraffins, including isomers thereof; petroleum fractions; mineral oil; kerosene; aromatic hydrocarbons such as toluene, xylene, and naphthalene, including hydrogenated derivatives thereof such as decalin and tetralin; halogenated hydrocarbons such as monochlorobenzene; cycloalkanes or cycloalkenes such as careen, fluorine, camphene, menthane, dipentene, naphthalene, acenaphtalene, methylcyclopentandien, tricyclodecane, 1,2,4,5-tetramethyl-1,4-cyclohexadiene, fluorenone, naphtindane, tetramethyl-p-benzodiquinone, ethylfuorene, fluoranthene and naphthenone.
[24] The method of any one of embodiments [21]-[23], wherein the spin solvent is relatively volatile, like decalin or tetralin; preferably the spin solvent is decalin.
[25] The method of any one of embodiments [21]-[24], wherein the spin solvent is removed by evaporation, by extraction, or by a combination of evaporation and extraction routes, preferably spin solvent is removed to a residual level of at most 500, 400, 300, 200, 100 or 60 ppm.
[26] The method of any one of embodiments [21]-[25], wherein the spin mixture is prepared by mixing the components with spin solvent using equipment like a high-speed mixer at ambient temperature, to make a dispersion of at least polyolefin and bioceramic particles in spin solvent.
[27] The method of embodiment [26], wherein the polyolefin is dissolved in the spin mixture by using a higher temperature.
[28] The method of any one of embodiments [21]-[27], wherein the spin mixture is homogenized and polyolefin is dissolved in the spin solvent in a twin-screw extruder operated at a temperature of 150-300° C., and then spun through the orifices into an air gap, the fibers formed are then cooled in a quench bath to solidify into gel fibers, and the gel fibers are drawn before, during or after removing at least a part of the spin solvent.
[29] The method of any one of embodiments [21]-[28], wherein drawing is carried out in multiple, preferably uniaxially drawing steps, at increasing temperatures.
[30] The method of any one of embodiments [21]-[29], wherein multiple drawing steps are applied for a UHMWPE-based fiber with a total draw ratio of up to 10 for drawing temperatures up to 120° C., a total draw ratio of up to 25 for drawing temperatures up to 140° C., and a total draw ratio of 50 or above for drawing temperatures up to and above 150° C. in the final stage of drawing.
[31] The method of any one of embodiments [21]-[30], wherein the composite fibers or yarns made have a tenacity of at least 15.0 cN at low spin solvent content.
[32] The method of any one of embodiments [21]-[31], wherein the bioceramic particles are added by feeding as dry powder or as a dispersion in spin solvent to an extruder processing the polyolefin and spin solvent to result in a dispersion of the particles in a polyolefin solution.
[33] The method of any one of embodiments [21]-[32], further comprising a step of post-treating the surface of the fibers obtained, to at least partly remove a polyolefin layer from the fiber surface and/or from bioceramic particles present in the surface layer of the fiber body, to result in composite fibers with an increased level of bioactivity.
[34] The method of embodiment [33], wherein the post-treatment step includes contacting the surface of fibers with a solvent for the polyolefin, or plasma etching the surface of fibers in an oxygen-containing atmosphere.
[35] A multi-filament yarn that comprises 1) the composite fibers of any one of embodiments [1]-[20] or as obtained with the method of any one of embodiments [21]-34] and 2) up to 50 mass % of other fibers based on biocompatible polymers, including fibers with lower amounts of bioceramic particles or without bioceramic particles; preferably the yarn comprises at most 40, 30, 20 or 10 mass % of other fibers.

[36] A multi-filament yarn that substantially consists of the composite fibers of any one of embodiments [1]-[20] or as obtained with the method of any one of embodiments [21]-[34]

[37] The multi-filament yarn of embodiments or [36], having a tensile strength or tenacity of at least 15, 20, 25, 28, 30, or 32 cN/dtex.

[38] The multi-filament yarn of any one of embodiments [35]-[37], having a tensile modulus of at least 600, 800, 900, or 1000 cN/dtex as measured with a method following ASTM D885M.

[39] The composite fibers of any one of embodiments [1]-[20] or the multi-filament yarn of any one of embodiments [35]-[38], wherein the fibers have a surface coverage by exposed bioceramic particles of 0.1-35 area %, as determined with XPS analysis and normalized to a HA surface; or have a surface coverage by exposed bioceramic particles of 0.1-35 area % as determined with AFM surface analysis.

[40] The composite fibers or yarn of embodiment as directly obtained by a gel-spinning process and comprising up to 20 mass % of HA, wherein said surface coverage is in the range of 0.5-6 area %.

[41] The composite fibers or yarn of embodiment as obtained after applying a plasma etching step as post-treatment and comprising up to 20 mass % of HA, wherein said surface coverage is at least 0.2, 0.5, or 1 area %, and at most 30, 25, 20, 15, 10 or 8 area %.

[42] The composite fibers of any one of embodiments [1]-[20] or the multi-filament yarn of any one of embodiments [35]-[38], wherein the fibers show at least 25% higher ALP activity after 28 days in an ALP assay than corresponding fibers containing no bioceramic particles, preferably the fibers show at least 30, 40, 50, 60, 70, 80, 90, 100, 150 or even 200% higher ALP activity after 28 days in an ALP assay.

[43] A fibrous article comprising the composite fibers or yarn as disclosed in any one of embodiments [1]-[42], and optionally other biocompatible fibers that do not show similar bioactivity or other biocompatible materials.

[44] The fibrous article of embodiment [43], wherein at least those parts of the fibrous article that should show bonding to (bony) tissue when used as a medical implant contain at least 50, 60, 70, 80 or 90 mass % of the bioactive composite fibers or yarn.

[45] A fibrous article substantially consisting of or consisting of the composite fibers or yarn as disclosed in any one of embodiments [1]-[42].

[46] Use of the fibrous article of embodiments [43]-[45] as a biomedical implant or as a component of a biomedical implant, preferably the implant is a permanent high-strength orthopedic implant for repairing bone fractures or torn ligaments or tendons, like a flexible tissue anchor, cortical fixation device like an ACL loop, a high-strength orthopedic suture, a transosseous cerclage cable, a synthetic tendon or ligament graft, an interspinous spacer or spinal disc prosthesis, a spinal fusion device, or a synthetic scaffold to repair bone voids.

[47] A biomedical device or implant comprising the composite fibers or yarn as disclosed in any one of embodiments [1]-[42] or the fibrous article of embodiments [43]-[45].

Experiments

Methods

IV: the Intrinsic Viscosity of UHMWPE is determined according to method ASTM D1601 (2004) at 135° C. on solution in decalin, the dissolution time being 16 hours, with BHT (butylhydroxytoluene) as anti-oxidant in an amount of 2 g/l solution, by extrapolating the viscosity as measured at different concentrations to zero concentration.

Tensile properties of yarns: tenacity and modulus are defined and determined on multifilament yarns as specified in ASTM D885M and ASTM D2256M, using a Zwick Z005 tensile machine with Instron Clamps 21714-044. A S-twist with 100 tpm was introduced to the yarn before testing. The tensile measurements were performed with a 5 kN load cell at a crosshead speed of 250 mm/min with a gauge length of 500 mm. The mean linear density was calculated from the mass of 100 m of the yarn, following ASTM D1907M. Reported values are the average of 5 individual tensile determinations for each sample.

Knot pull-out strength (also called knot slip strength) was tested on braids, using a Zwick Z005 Universal Testing Machine with Instron Clamps 2714-044, equipped with a 5 kN load cell. In this test setup, a surgeon's knot was made in the middle of a braid, and a preload of 53 N was applied at a cross-head speed of 50 mm/min. This knot tends to slide out rather than tighten on itself when tension is applied to the ends of the braid. Surgeon's knots are commonly used for suturing tissue in clinical applications, so this test aims to model the tendency of braided constructions to stay tightened under tension. The knotted loop was cut in the middle and the two new legs were mounted in the test clamps with the knot in the middle, spaced 200 mm apart. A constant cross-head speed of 100 mm/min was applied until yield. The reported value is the force at this yield point, averaged for 10 tests.

Particle size of bioceramic particles was measured on particles dispersed in decalin, with a Malvern Mastersizer 2000 and applying Fraunhofer particle size analysis method.

Inorganic particles content of composite fibers was determined by ash testing according to ISO 13451-1:2008. The tests were performed in duplicate with incineration at 750° C. for 3 hours. All ash residues were assumed to be inorganic material. Fiber samples from different stages in the processes, i.e. after different drawing steps as well as after textile converting (braiding) were analyzed to check if the fibers lost any particles by e.g. abrasion during the processes.

The coefficient of friction (CoF) of UHMWPE fibers containing HA or a mixture of HA and bTCP were evaluated using Honigmann HCC μ-meter equipment. Two test set-ups were performed on the fibers: (1) yarn on yarn (Y—Y) CoF and (2) yarn on solid CoF (Y—S, steel pin hardened with roughness value 0.1 μm); both at 1 and 10 m/min.

FTIR spectra were recorded with a Perkin-Elmer Spectrum 100 FTIR Spectrometer with the Zn/Se crystal attenuated total reflectance (ATR) mode. At least 4 scans with a spectral resolution of 4 cm-1 were averaged in the range of 4000-400 cm-1.

The surface morphology of composite fibers was examined using a FEI Versa 3D FEG scanning electron microscope (SEM) to evaluate possible morphological differences between fibers with different bioceramic particle loading. Samples were sputter-coated with carbon and SEM images were captured with an acceleration voltage of 5 kV.

AFM measurements were carried out on a MM8 Bruker system equipped with a NanoScope V controller. A Si-made cantilever was used having a force constant of about 40 N/m and the Si-curvature was about 10 nm. AFM was applied in tapping mode to record both topography and phase-contrast images, and the phase-contrast image was related to the local surface mechanical or chemical difference. By AFM tapping mode, the AFM tip is not in contact with the sample surface under a light tapping force. For calculating relative surface coverage on fiber surface by bioceramic particles, the AFM images were converted into black-white images, which were then analyzed by customized image analysis software.

XPS measurements were carried out on a Quantera Hybrid from Ulvac-PHI (Q1 and Q2); using monochromatic AlKα-radiation and a take-off angle θ of 45°. At this angle, the information depth is approximately 7 nm. The polymer samples were measured in HS mode with a spot size of 1200×500 µm². The powders were measured using a spot size of 100 µm. Survey-scans were recorded to identify the elements present at the surface. Accurate narrow-scans have been measured for quantification.

SEM-EDX investigation was performed on a Versa 3D HR FEG-SEM equipped with an Everhart Thornley Detector (ETD, topography information), a Concentrical Back Scatter Detector (CBS, materials contrast information) and an EDAX TEAM elemental analysis detector at accelerating voltages of 5-10 kV.

Alizarin Red (1,2-dihydroxyanthraquinone; Sigma) colorant was reconstituted into a dye solution according to the supplier's instructions. In short, the solution was prepared by dissolving approximately 6.85 g of powder in 500 ml deionized water. The pH was adjusted to 4.2 by adding 1M NaOH. The final solution was then filtered through a 0.2 µm pore size membrane. The samples were immersed in the solution for 10 min at room temperature and then thoroughly washed under tap water until all nonspecific staining had been removed.

Cell culture experiments: human mesenchymal stromal cells (hMSCs; Lonza, PT2501, 22 year/old male) were thawed at passage 02 and cultured in basic cell culture medium (Lonza PT-3238) in a P225 culture flask (VWR). Medium was refreshed after 2 and 4 days. At day 7, the cells were sub-passaged into 2 new T225 cells (passage 03). Medium was refreshed after 2, 4 and 7 days. At day 9, the cells were used for the experiment at passage 04. For cell culture, untreated multi-well culture plates (48 wells) were used to decrease cell adhesion to the culture plate rather than the test samples. All materials were incubated in 300 µl basic cell culture medium (Lonza, PT-3238) overnight prior to cell seeding. The test materials were fixed to the bottom of the 48-well plates using cell crowns (Sigma-Aldrich). After incubation, cell culture medium was removed, followed by cell seeding directly on the surface of each sample at a density of 20,000 cells in 50 µl basic cell culture medium. The well plates with samples and cells were incubated at 37° C. in a humidified atmosphere with 5% $CO_2$. After 4 hours of incubation, 250 µl of basic or mineralization medium was added to the wells. Cells were cultured on materials for 7, 14 or 28 days, with complete medium refreshment (300 µl) at day 3, 5, 7, 10, 12, 14, 17, 19, 21, 24, and 26.

Cell morphologies on the various test samples were analyzed using SEM. The cells were first washed with phosphate buffer solution (PBS) and dehydrated by subsequent immersion in 50%, 60%, 70%, 80%, 90%, 96%, 96% and 100% of ethanol, 30 minutes per step. They were then dried using a critical point dryer. Prior to SEM analysis, the samples were attached to a stub using conductive double-sided carbon tape or conductive silver paint, and sputter coated with a nano-layer of gold or iridium. Micrographs were taken using the FEI Teneo SEM. Two (n=2) replicate test samples were analyzed at day 28.

Biochemical assays: cell proliferation and osteogenic differentiation were evaluated using DNA and alkaline phosphatase (ALP) enzyme activity assays, respectively. DNA content is representative of cell number at a given time point, and ALP activity is an early marker of osteogenic differentiation. DNA content and ALP activity were measured in the cell lysate of n=4 replicate test samples per time point. Assay measurements were performed in duplicate per test sample.

For biochemical assays, cells were lysed as follows: at each time point, test samples were removed from their culture wells and transferred to wells of a fresh multi-well plate. Samples were then frozen for 1 hour at −30° C. and thawed at room temperature. Cyquant cell lysis buffer (Cyquant Assay, component C7026; cell lysis buffer 20× diluted in NaCl-EDTA (180 mM NaCl/1 mM EDTA) containing RNase was added to each test sample well (250 µL) and incubated for 1 hour at room temperature before sampling for DNA and ALP assays.

DNA assay: to measure DNA content, the CyQuant (Thermo Fisher Scientific) was used following the manufacturer's instructions. A standard curve was made from 0 to 0.35 µg/µl DNA (λDNA) diluted in lysis buffer+RNase to a final concentration of 10 µg/ml. 100 µl of cell lysate was pipetted into wells of a white 96-well plate, followed by the addition of 100 µl GR-dye solution (GR-dye 200× diluted in Cyquant cell lysis buffer) and mixing. The well plate was then incubated for 15 minutes in dark at room temperature before the analysis. Readout (BMG labtech Clariostar plate reader): Emission 500 nM; Excitation 480 nM.

ALP assay. ALP activity was measured using the CDP star assay (Roche 12041677001) following the manufacturer's instructions. 10 µl of cell lysate was pipetted in the wells of an opaque 96-well plate to which 40 µl of CDP star solution was added, followed by incubation in dark at room temperature for 40 minutes. Readout (BMG labtech Clariostar plate reader): luminescence (denoted "Lum").

Cell viability: to assess the metabolic activity of cells, Presto Blue Assays were performed. Cells were cultured in quadruplicate and the experiment was performed in duplicate (i.e. 8 experimental samples for each group were included). Samples and HA discs were taken out of the 48-well plate and placed in a new 48-well plate. After washing cells with PBS, 500 µl of a solution of Presto Blue in basic medium (dilution 1:10) was added to the cells. Incubation time was 30 minutes at 37° C. Then, 200 µL of this solution was transferred to wells of a white 96-well plate for the analysis. Readout (BMG Abtech Clariostar plate reader): Emission: 590 nM; Excitation: 545 nM (denoted in relative fluorescent units, "RFU").

Preparation and Property Evaluation of UHMWPE Fibers
Dispersions of Bioceramic Particles Hydroxyapatite powder (HA) was obtained from Premier Biomaterials Ltd (PurAtite™ HA; $Ca_{10}(PO_4)_6(OH)_2$; indicated to be spherical particles with particle size D50 of 0.7 µm). Beta-tricalcium phosphate powder (bTCP) was obtained from Premier Biomaterials Ltd (BTCP 1; $Ca_3(PO_4)_2$; indicated to be spherical particles with particle size D50 of 2.7 µm). Dispersions of the inorganic particles in decalin at 10 mass % loading of particles based on the dispersion were made by mixing the particles as received with decalin (decahydronaphthalene; Evonik Industries AG) and 0.015 mass % of surfactant (Statsafe® 6000) in a stainless-steel vessel at room temperature and at 10.000 rpm during 5 minutes, using Ultra-Turrax® T50 and G45F dispersing equipment. Note that bTCP was used as mixtures of HA and bTCP in 80/20 and 60/40 mass ratios.

Some characteristics of the dispersions made are listed in Table 1. Particle sizes as observed on the dispersions are higher than the particle size as indicated by the suppliers of the inorganic particles. Apparently, there is (still) a certain degree of aggregation of primary particles in the decalin dispersion medium. Nevertheless, the visually homogeneous dispersions were observed to show good stability during at least 2-4 weeks. It was further anticipated that shear forces during the extrusion step in the fiber spinning process may induce a reduction in particle size.

TABLE 1

| Dispersion sample | Concentration of particles (mass %) | Particle size distribution (µm) | | |
|---|---|---|---|---|
| | | D10 | D50 | D90 |
| HA 100 | 10.0 | 2.3 | 4.7 | 39.0 |
| HA/bTCP 80/20 | 10.0 | 2.2 | 4.6 | 51.2 |
| HA/bTCP 60/40 | 10.0 | 2.2 | 4.7 | 50.2 |

Fiber Spinning and Tensile Properties

Comparative Experiment 1

Multi-filament UHMWPE yarn was made by a gel-spinning process wherein a 7.7 mass % slurry of UHMWPE powder of IV 23 dl/g in decalin was fed to a twin-screw extruder heated at 210° C., the resulting solution was spun via a spinneret having 50 holes of 1 mm diameter into solution filaments, which filaments passed an air gap and were quenched in a water bath to form gel filaments. The gel filaments were further passed through hot air ovens during which water and decalin was evaporated, while drawing the filaments to result in a 50-filament yarn with titer 128 dtex.

In Table 2 several characteristics and tensile properties of this yarn are collected.

Examples 2-6

Composite yarns were made with a process similar to that of CE1, but wherein the starting UHMWPE slurry was made by replacing part of the decalin by the particle dispersions listed in Table 1; aiming at a particles content of about 10, 15 or 20 mass % (based on total mass of UHMWPE and bioceramic particles) in the resulting composite multi-filament yarn. The spinning processes were stable, and products could be made without yarn breakage during up to 24 hours (experiments then stopped).

Ash residues measured on yarn samples obtained from different stages of the spinning process showed same results within experimental error. The data provided in Table 2 show that observed particle loadings in the yarns obtained were also in good agreement with the concentrations in the feed, indicating that the particles were incorporated within the UHMWPE filament bodies. Table 2 further shows that tensile properties are somewhat reduced by addition of the bioceramic particles, but tenacity is still on a high-strength level. In this respect, it should also be realized that a substantial amount or volume of UHMWPE is replaced by particles that will not contribute to the strength of the filaments and yarn; but might even hamper polymer orientation and crystallization in the filament, or act as stress concentrator or breakage initiator. Note that at a loading of 20 mass % about 8 vol % of the polyethylene in a filament will be replaced by the particles. Also the size of particles, D50 of about 5 µm as measured on the decalin dispersions, might have a negative effect; further optimization may be possible by reducing particle sizes.

Comparative Experiment 7

A composite yarn comprising 20 mass % of bismuth trioxide particles was made with a gel-spinning process as in WO2012/076728 and similar as described above for bioceramics. Tensile properties as listed in Table 2 for CE 7 and Ex 2 are comparable; both fibers also contain about the same vol % of inorganic particles.

TABLE 2

| Sample yarn | Type of particles | Particles in feed (mass %) | Ash residue (mass %) | Titer (dtex) | Tenacity (cN/dtex) | E-modulus (cN/dtex) | Elongation at break (%) |
|---|---|---|---|---|---|---|---|
| CE 1 | none | — | | 110 | 37.6 | 1342 | 3.3 |
| Ex 2 | HA | 10 | 9.4 | 119 | 29.5 | 1137 | 3.0 |
| Ex 3 | HA | 15 | 13.8 | 126 | 25.9 | 923 | 3.0 |
| Ex 4 | HA | 20 | 19.5 | 130 | 24.2 | 649 | 3.3 |
| Ex 5 | HA/bTCP 80/20) | 20 | 18.8 | 127 | 22.1 | 766 | 2.9 |
| Ex 6 | HA/bTCP 60/40) | 20 | 19.0 | 127 | 23.3 | 851 | 2.9 |
| CE 7 | $Bi_2O_3$ | 20 | 19.5 | 135 | 30.0 | 1067 | 3.2 |

Fiber Characterization
• Morphology

Figure 1B:
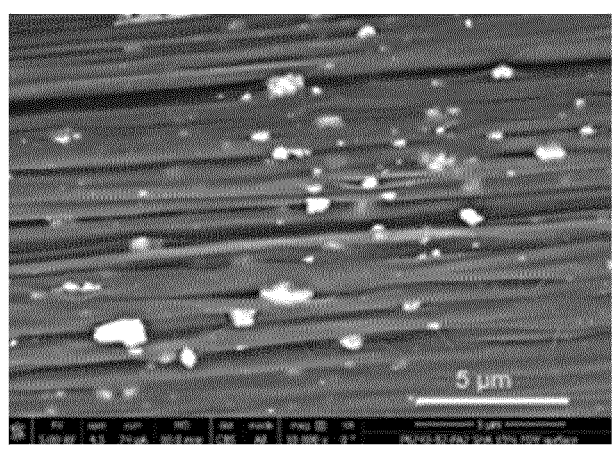
Figure 1C:
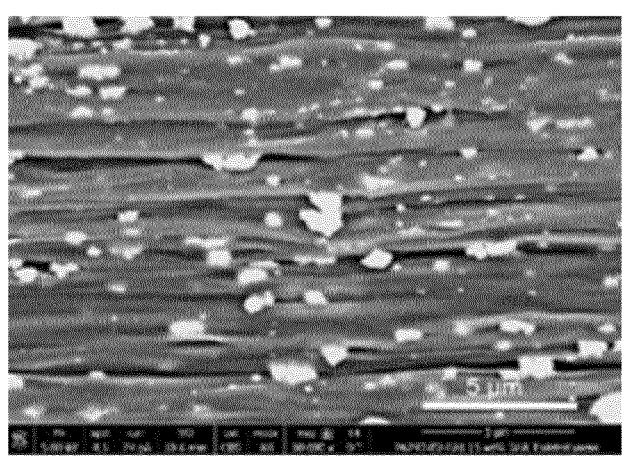
Figure 2A:
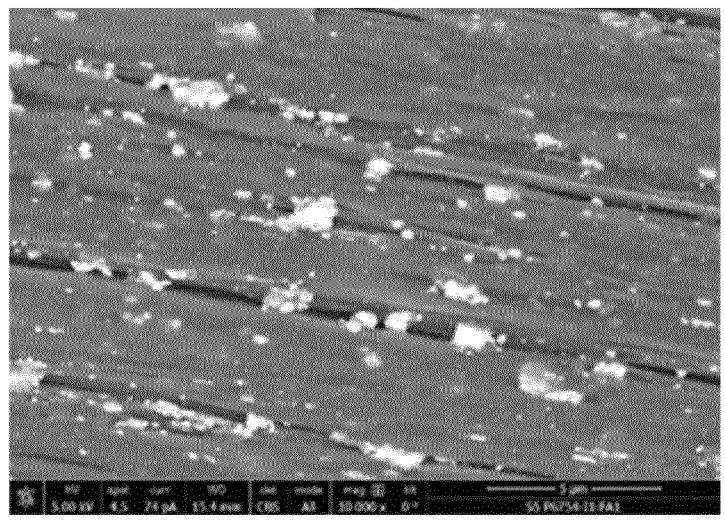
FIGS. 2A and 2B show SEM micrographs for composite fibers containing 20 mass % of HA/bTCP mixtures
Figure 2B:
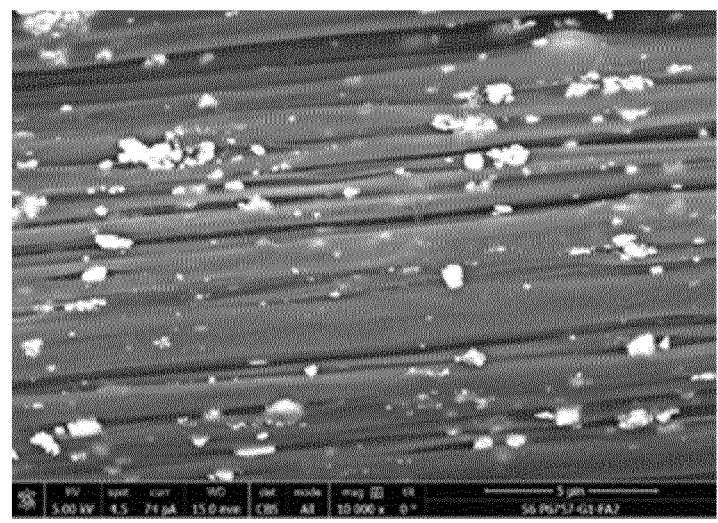

The surface of fibers was investigated with SEM. In FIGS. 1 and 2 several SEM micrographs are reproduced for examples Ex 2-4 (FIGS. 1A-1B-1C) and Ex 5-6 (FIGS. 2A-2B), wherein bioceramic particles are visible at the surface of twisted drawn yarns as light colored features. There appears to be a positive relation between the number of said features and amount of particles used in making the fibers. No significant difference is apparent between HA and bTCP particles. In general, there are indications that particles at the surface layer of fibers are not fully embedded in or not fully covered by polyethylene; but that they are at least partly exposed to their environment. This conclusion was supported by further SEM experiments wherein acceleration voltages were varied from 2 to 20 kV in the SEM imaging; revealing more distinct white features at 10 and 20 kV likely resulting from larger penetration depth. Note that a typical penetration depth with SEM techniques is on the order of 1 µm, dependent on conditions used.

SEM micrographs were also made of filament cross-sections of the various samples. Particles appeared distributed and embedded throughout the filament cross-section including the edges and showed some variation in degree of primary particle aggregation. Apparently shear forces during mixing and spinning were not enough to completely break up the aggregates present in dry particles.

Similarly, surfaces of braided and knitted constructions made from composite fibers were evaluated with SEM (see later). It was concluded therefrom that the fiber or filament surface was not noticeably affected by braiding and knitting operations.

• Surface Properties

Because particles being present in or at a surface layer of filaments might result in different surface roughness of filaments and yarn, coefficient of friction (CoF) was measured for composite fibers and neat UHMWPE fibers. The CoF is a dimensionless scalar that describes the ratio of the force necessary to keep the contact areas moving and the force needed to press them together; CoF ranges from 0 to greater than 1 dependent on the material tested. Results collected in Table 3 indicate that addition of bioceramic particles increases the yarn-to-yarn (Y—Y) CoF; suggesting a rougher surface. Such trend is less apparent for measured yarn-to-solid (Y—S) CoF values. At 10 mass % HA loading the difference in Y—S CoF versus unloaded fiber was very small, suggesting that only few particles are present at the surface. In contrast, the Y—S CoF value increased significantly for composite fibers containing 20 mass % of HA/bTCP.

TABLE 3

| Sample | Yarn-to-Yarn CoF | | Yarn-to-Solid CoF | |
| --- | --- | --- | --- | --- |
| | At speed 1 m/min | At speed 10 m/min | At speed 1 m/min | At speed 10 m/min |
| CE1 | 0.16 ± 0.02 | 0.17 ± 0.03 | 0.07 ± 0.01 | 0.09 ± 0.02 |
| Ex 2 | 0.19 ± 0.02 | 0.19 ± 0.05 | 0.07 ± 0.01 | 0.09 ± 0.02 |
| Ex 3 | 0.21 ± 0.03 | 0.22 ± 0.03 | 0.09 ± 0.01 | 0.11 ± 0.02 |
| Ex 4 | 0.23 ± 0.03 | 0.23 ± 0.04 | 0.10 ± 0.01 | 0.11 ± 0.02 |
| Ex 5 | 0.23 ± 0.03 | 0.24 ± 0.04 | 0.11 ± 0.02 | 0.20 ± 0.02 |
| Ex 6 | 0.23 ± 0.03 | 0.23 ± 0.04 | 0.17 ± 0.02 | 0.21 ± 0.05 |

Figure 3:
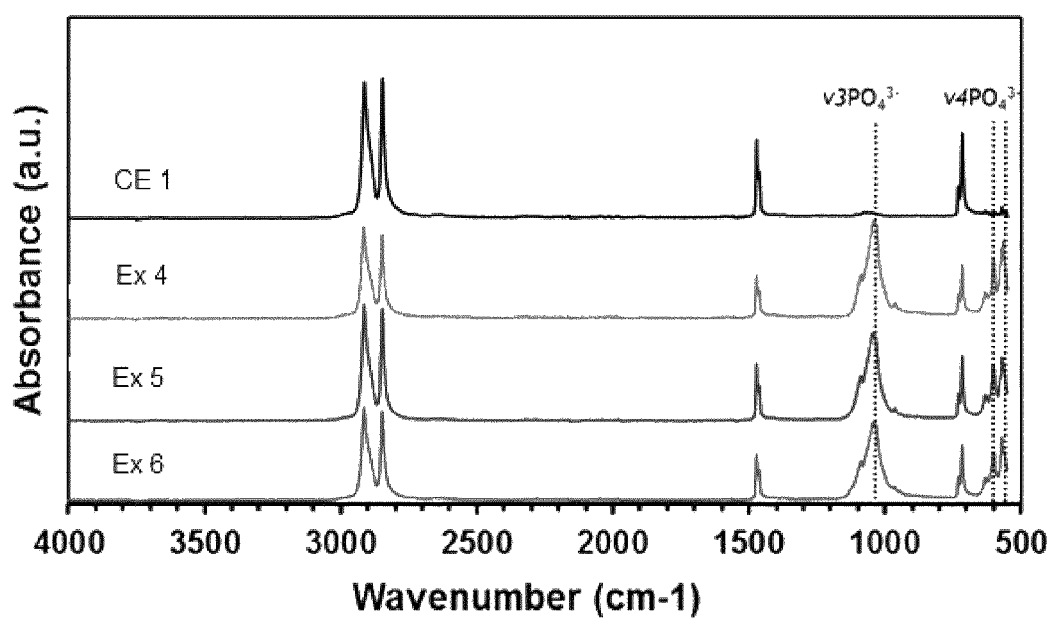
FIG. 3 shows FTIR spectra for fibers with 0 and 20 mass % of bioceramic particles.

The chemical compositions of bioceramic loaded UHMWPE fibers were analyzed by FTIR-ATR spectroscopy and compared to neat (unloaded) UHMWPE fibers. The same IR bands were observed for all the bioceramic loaded fibers, but peak intensities varied; see FIG. 3. The band at 1005 cm$^{-1}$ is attributed to the $v_3(PO_4^{3-})$ and those at 602 and 559 cm$^{-1}$ are attributed to the $v_4(PO_4^{3-})$. These signals clearly originate from the bioceramic particles (HA and bTCP), as they are not found for neat UHMWPE fibers. This FTIR-ATR technique has a penetration depth of between 0.5 and 5 µm, so it cannot be excluded that the bioceramic particles are covered with a thin layer of UHMWPE; instead of being freely exposed at the fiber surface.

Preparation and Property Evaluation of Fibrous Articles
Braiding and Knitting

Braided constructions comprising 16 strands were made from the yarns obtained from CE1 and Ex 2-6, using Herzog TT78 braiding equipment and a single yarn for each strand, and a stich level of 15 stitches per cm. The resulting braids had a size similar to a standard size USP2 suture.

Knitted constructions were also made from the various yarns, to make flat fibrous constructions that are more suitable as substrate for in vitro testing and subsequent evaluation. A Shima Seiki N.SFG-10 L/M MGF No. 20922 knitting machine was used to make constructions by plain stitches, gauge 10, using 78 needles and fixed loop length.

Knot Pull-Out

Knot pull-out strength, also called knot slip strength, was measured on braids made from neat UHMWPE yarn (CE 1), from bismuth-oxide containing yarn (CE 7), and from yarn comprising 10 and 20 mass % of HA particles (Ex 2 and 4). Knot pull-out strength was markedly higher for the braids made from HA-containing fibers; as shown in Table 4. This increase in pull-out strength represents an important advantage in orthopaedic applications of the yarns, as slip knots are frequently used in sutures and other (braided) cables in such surgery.

TABLE 4

| 16-strand braid made from | Knot pull-out strength (N) |
| --- | --- |
| CE 1 yarn (no HA) | 14 ± 5 |
| Ex 2 yarn (10 mass % HA) | 27 ± 10 |
| Ex 4 yarn (20 mass % HA) | 43 ± 7 |
| CE 7 yarn (20 mass % Bi$_2$O$_3$) | 19 ± 6 |

Surface Treatment and Characterizations
• Plasma Etching

The outer surface of fibers in braided and knitted samples were plasma etched at EMPA, Swiss Federal Laboratories for Material Science and Technology. The treatments were performed in a pilot web coater using a reel-to-reel system. The fibrous articles were wound around a drum electrode within a RF-driven reactor (width of 65 cm, diameter of 59 cm). Prior to plasma etching the bioceramic-loaded UHMWPE samples, suitable etching rates were estimated by using polyolefin foils (LDPE and PP). The conditions subsequently applied to the samples (40 min, Ar/O$_2$ plasma, 160/40 sccm, 1000 W, 1 mbar) were found to result in an etching rate of about 25 nm/min. It was anticipated that the samples would be predominantly etched on the side not in contact with the drum electrode.

• SEM and AFM

Figure 4A:
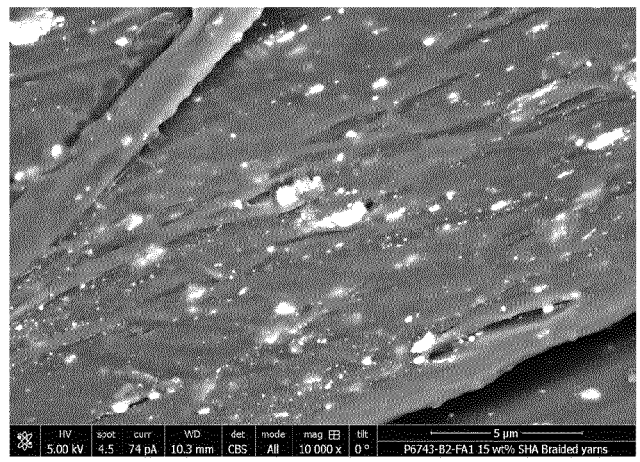
FIGS. 4A, 4B, 5A and 5B show SEM and AFM images, respectively, for composite fibers with 15 mass % of HA, before and after plasma etching.
Figure 4B:
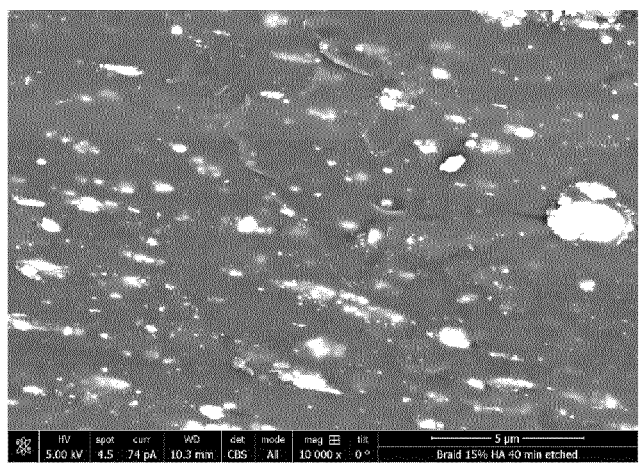

Before and after etching the surfaces of samples, braids were examined with SEM. The braids were fixed with double-sided adhesive carbon tape to a SEM sample holder and coated with a conductive carbon layer. Imaging was done at 5 kV in a FEI Versa 3D FEG SEM. In FIG. 4 representative examples of micrographs are shown for a braid made from Ex 3 fibers loaded with 15 mass % of HA, before (FIG. 4A) and after plasma etching (FIG. 4B).

Similar results were obtained for the other braids before and after plasma etching. There appear to be more particles visible as white spots after etching; particles appear to have sharper edges and to be of larger size and to protrude more from the surface. As the etching step will have resulted in removing polyethylene from a surface layer of about 1 μm thickness, this confirms that SEM has a penetration depth of also about 1 μm and shows at least part of bioceramic particles in a such layer also before plasma etching. Note that the etched sample in FIG. 4B shows a more fibrillar surface, likely resulting from polyethylene being etched away.

Figure 5A:
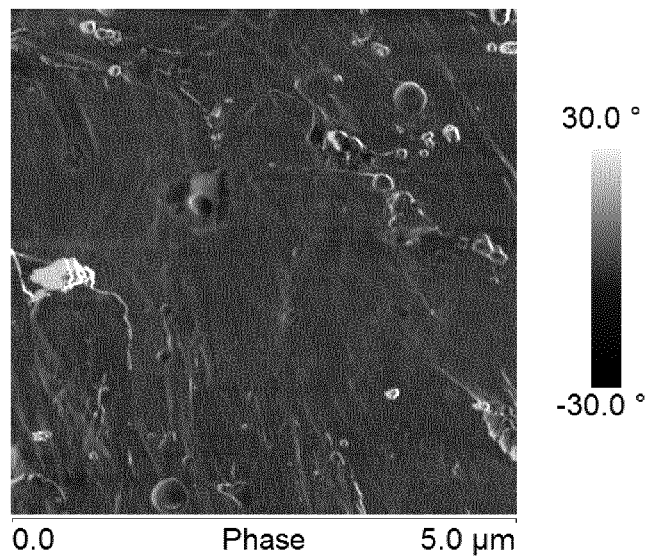
Figure 5B:
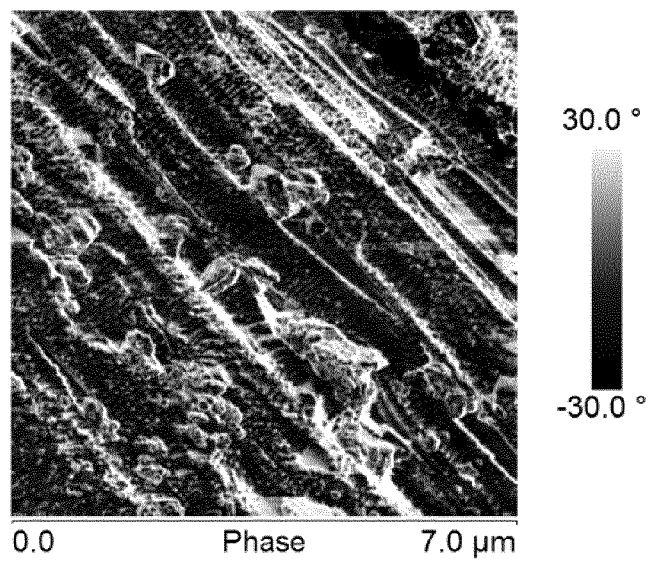

The above discussed changes show even more pronounced on images recorded with AFM, which technique scans only the true surface; see FIG. 5. FIG. 5A shows the surface of the braid made from Ex 3 fibers without plasma etching and FIG. 5B shows the surface after the plasma etching step. In addition to more exposed particles, the image also appears to show more detail on polyethylene filament level.

• XPS and AFM

The chemical compositions of the composite bioceramic/UHMWPE fibers were characterized with both XPS and AFM. AFM provides a direct indication of the amount of exposed bioceramics at the surface of a fiber, as a clear distinction can be made between hard (bioceramic) and a relatively softer (polyethylene) phases. XPS is used to measure the atom % of calcium and phosphor in the top layer (defined as approximately 7 nm).

From XPS results (see Table 5) a surface coverage by HA particles of a few percentage is deduced. Surface coverage was calculated as area % relative to a 100% hydroxyapatite particles as reference, from the (Ca+P) atom % values for the fiber/braid samples. The plasma treatment appeared to significantly increase the surface coverage of bioceramic particles, and thus likely the number and/or area of exposed particles.

Figure 6:
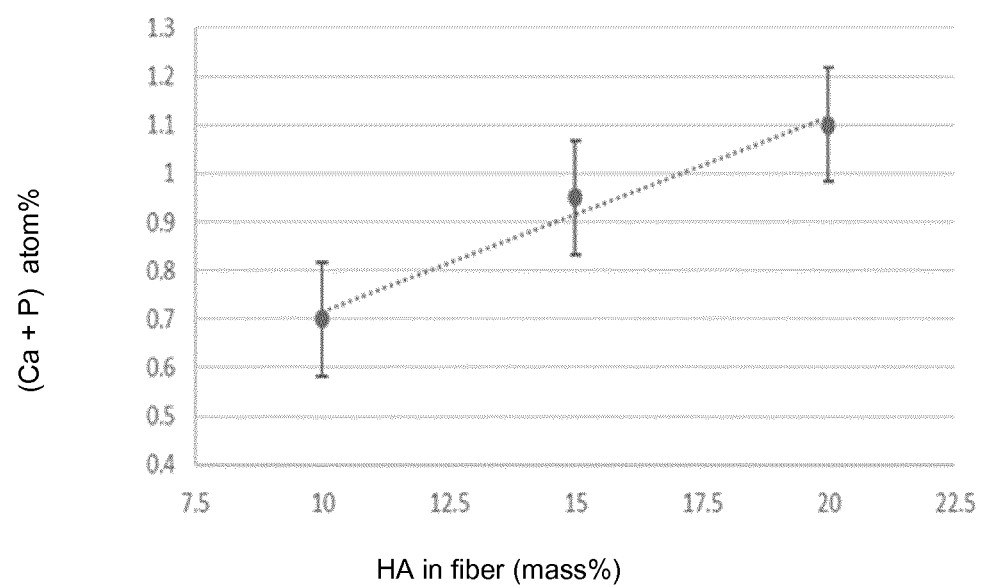
FIG. 6 shows XPS results for fibers with 10, 15 and 20 mass % of HA particles.
Figure 9A:
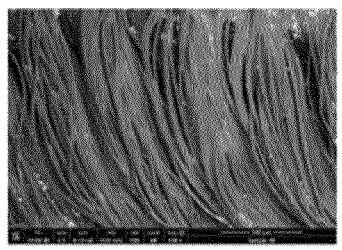
FIGS. 9A-9F show SEM images of fiber samples cultured with hMSCs for 28 days.
Figure 9C:
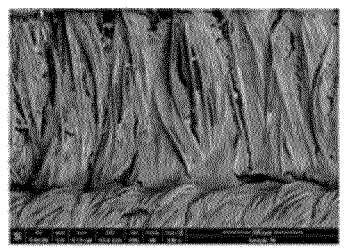
Figure 9E:
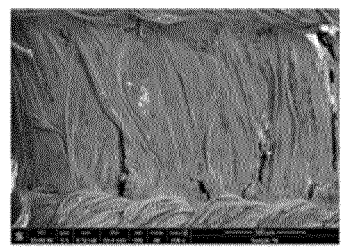
Figure 9B:
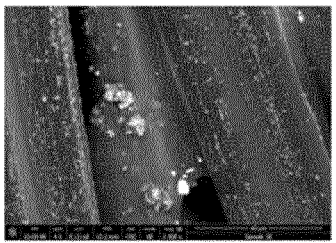
Figure 9D:
Figure 9F:
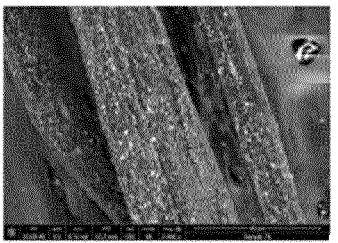

FIG. 6 shows an almost linear relation between measured (Ca+P) atom % and the amount of HA particles added to the fibers.

TABLE 5

| Sample | Ca (atom %) | P (atom %) | (Ca + P) (atom %) | Surface coverage (area %) |
|---|---|---|---|---|
| Braid made from CE 1 fibers | 0 | 0 | 0 | 0 |
| Braid made from Ex 2 fibers | 0.4 | 0.3 | 0.7 | 2 |
| Braid made from Ex 3 fibers | 0.6 | 0.4 | 1.0 | 3 |
| Braid made from Ex 4 fibers | 0.7 | 0.5 | 1.1 | 4 |
| Braid made from Ex 5 fibers | 0.9 | 0.7 | 1.6 | 5 |
| Braid made from Ex 6 fibers | 0.7 | 0.6 | 1.3 | 4 |
| Plasma-treated braid made from Ex 3 fibers | 3 | 2 | 5 | 16 |
| HA particles | 18 | 13 | 31 | 100 |

AFM measurements on the braids made from HA-loaded fibers of Ex 2-4 also provide indication for the relative surface area of bioceramic particles at the surface of fibers. In Table 6 results are summarized (rsd=relative standard deviation; n is the number of different spots measured). The AFM surface coverage values are somewhat lower, as the penetration depth is smaller compared to XPS, but still are of the same order as derived from XPS experiments.

In general, the exposed bioceramic particles at the surface of fibers made with 10-20 mass % bioceramics are found to have a surface coverage in the range 0.7-5 area %, based on AFM and XPS results. This surface coverage can be significantly increased by a plasma treatment; for example to about 16-17 area % for fibers made with 15 mass % of HA.

TABLE 6

| | Surface coverage | | |
|---|---|---|---|
| Sample | (area %) | rsd | n |
| Braid made from Ex 2 fibers | 0.8 | 80 | 4 |
| Braid made from Ex 3 fibers | 0.7 | 55 | 5 |
| Braid made from Ex 4 fibers | 0.7 | 61 | 4 |
| Plasma-treated braid made from Ex 3 fibers | 17 | 70 | 3 |

• Alizarin Staining

Alizarin Red staining was used to visualize bioceramic particles in samples, because this is a well-known method to stain bone mineral; the dye having a high affinity for calcium. Knitted structures made from neat UHMWPE fibers (CE1) and from composite 15/85 HA/UHMWPE fibers (Ex 3) were treated with a solution of the red colorant alizarin red, which has affinity with the inorganic material but not with a polyolefin like UHMWPE. The knitted structure made from neat UHMWPE fibers indeed showed no noticeable coloring, whereas the structure made from the Ex 3 fibers showed some coloring; as shown in FIGS. 7 (7A and 7B, respectively). In FIG. 7C the knitted structure made from Ex 3 composite fibers is shown, after first plasma etching the structure and then exposing to alizarin red. In this case, virtually the whole structure is colored red, indicating much more HA particles were accessible for interacting with the colorant after plasma etching.

• In Vitro Cell Culture and Bioactivity

In Table 7 results are depicted for cell viability studies using the Presto blue assay, of hMSCs cultured on different materials for 28 days. Generally, an increase in cell viability was observed over time, which is indicative of cellular proliferation, and with increased bioceramic loading; but results for different samples appear to scatter somewhat.

Results from the ALP assays are also summarized in Table 8, showing ALP activity after 28 days for all tested knitted fabrics based on fibers containing bioceramic particles. ALP activity appears to increase with bioceramic particle loading; and was highest for the 15 mass % sample after plasma etching. The results of Presto blue and ALP assays at 28 days are also represented schematically in FIGS. 8A and 8B, respectively, and confirm said trends. The observed increase in ALP activity at 28 days as found in these ALP assays appears to be at least 60% versus non-loaded fibers for the fabric made from fibers containing 10 mass % of HA, and increases to over 250% for the plasma-etched sample containing 15 mass % of HA.

TABLE 7

| Sample | Cell viability at day 28 RFU (mean value ± std) | ALP activity at day 28 Lum (mean value ± std) |
|---|---|---|
| Knitted fabric made from CE 1 fibers | 455515 ± 5240 | 14319 ± 2412 |
| Knitted fabric made from Ex 2 fibers | 75353 ± 7007 | 23096 ± 6087 |
| Knitted fabric made from Ex 3 fibers | 104628 ± 15985 | 27301 ± 3392 |

TABLE 7-continued

| Sample | Cell viability at day 28 RFU (mean value ± std) | ALP activity at day 28 Lum (mean value ± std) |
|---|---|---|
| Knitted fabric made from Ex 4 fibers | 88356 ± 2487 | 28115 ± 5805 |
| Knitted fabric made from Ex 5 fibers | 108845 ± 8482 | 31042+ 2309 |
| Knitted fabric made from Ex 6 fibers | 116262 ± 13333 | 40538 ± 2853 |
| Knitted fabric made from Ex 3 fibers; plasma treated | 139720 ± 10452 | 51642 ± 10785 |
| HA disc | 25842 ± 7330 | 6890 ± 3533 |

• SEM-EDX

After culturing with hMSCs for 28 days, some knitted samples were also examined using SEM-EDX. Scanning electron microscopy showed that the bioceramic-loaded composite fiber samples were covered by more cells and cellular matrix than the unloaded fiber samples, in conformance with the cell viability data. Cell spreading, typified by long spindle-shaped cellular processes (filopodia) bridging between material filaments, also appeared to be enhanced by the composite fiber samples versus the unloaded control (see FIG. 9A-F, representing images for samples based on CE1 (FIGS. 9A-B) and Ex3 (FIGS. 9C-D) fibers, and the etched sample based on Ex 3 fibers (FIGS. 9E-F); at 2 magnifications). Electron-dense nodules (bright particulate-like features) were also observed to a greater extent on bioceramic loaded samples, such as 15 mass % HA plasma etched samples, which were not present at the beginning of the experiments and are morphologically distinct from the bioceramic particles loaded into the fibers (see FIGS. 2 and 4), suggesting biomineralization had occurred during the culture period.

Figure 10:
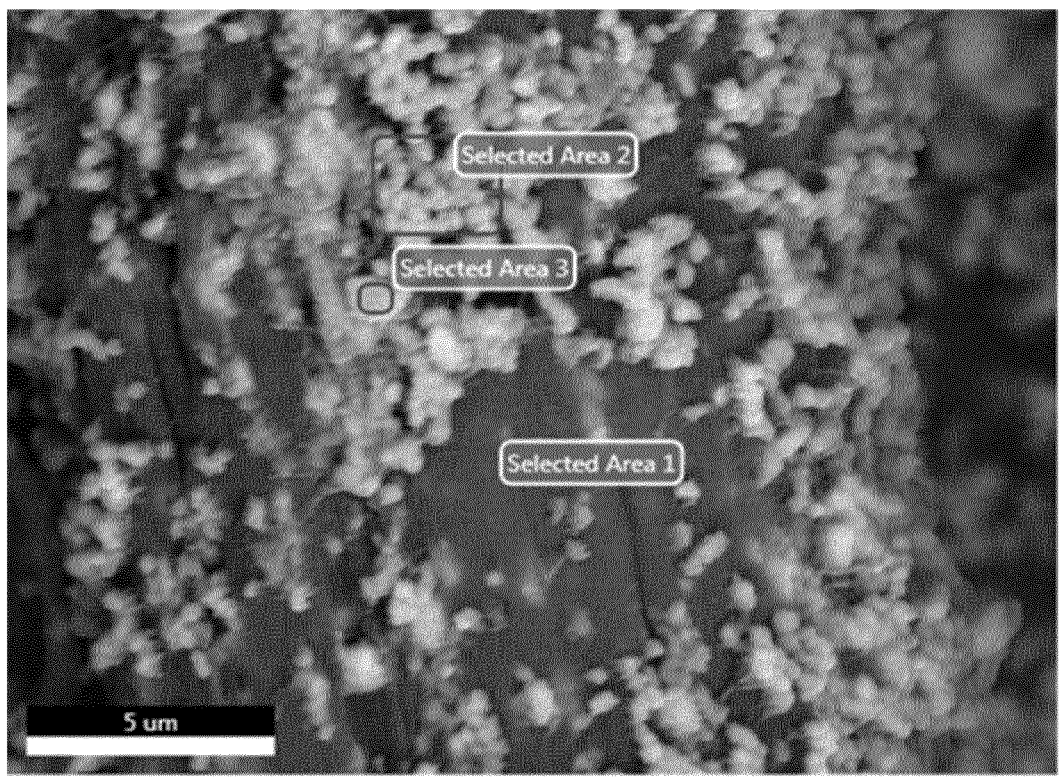
FIG. 10 represents a SEM-EDX image of the fiber surface of a knitted fabric made from fibers with 15 mass % of HA and plasma-etched, after 28 days culturing with hMSCs.
Figure 11:
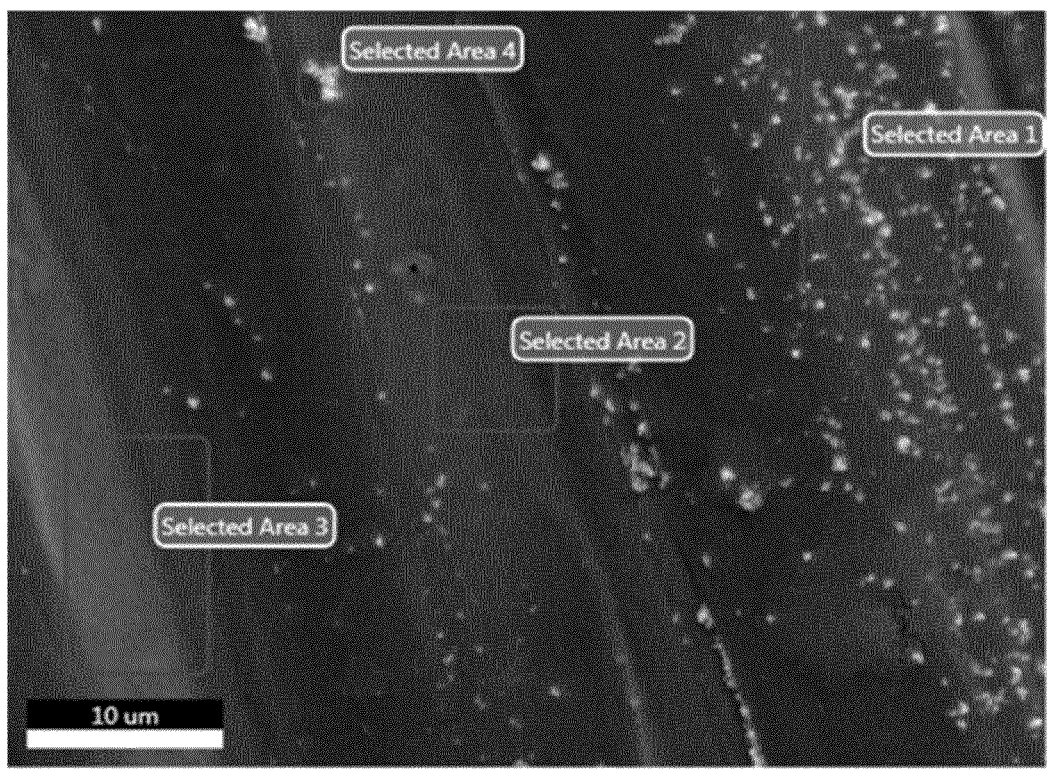
FIG. 11 represents a SEM-EDX image of the fiber surface of a knitted fabric made from unloaded fibers, after 28 days culturing with hMSCs.

Elemental analysis and mapping by SEM-EDX performed on nodules containing areas compared to areas without nodules formation (FIGS. 10 and 11, and Tables 8 and 9 providing results for the areas indicated in the images of FIGS. 10 and 11 respectively) showed an increase in Ca/C ratio and absence of other elements. Values are given as Net. Int.; indicating the net intensity of the signal measured as counts per seconds, corrected for baseline levels. Although EDX-quantification may not be straightforward, the results indicate that these nodules were composed of mainly calcium and phosphorous, thus confirming that biomineralization had occurred on the fiber (co-localized with carbon elemental mapping) as well as in the cellular matrix (co-localized with nitrogen elemental mapping and cellular morphology by SEM). Biomineral formation is an important readout of in vitro osteogenesis assays, because it is a key marker of the osteogenic differentiation of hMSCs into functional osteoblast-like cells. In vivo, biomineral formation is a necessary precursor to bone formation, a physiologic process that is mediated by mature osteoblasts (see e.g. Gentleman E., et al.; DOI: 10.1038/nmat2505). In contrast, biomineralized nodule formation on unloaded, neat fiber samples were considerably fewer and more dispersed (FIG. 11), correlating with low calcium and phosphate elemental signals.

Figure 12:
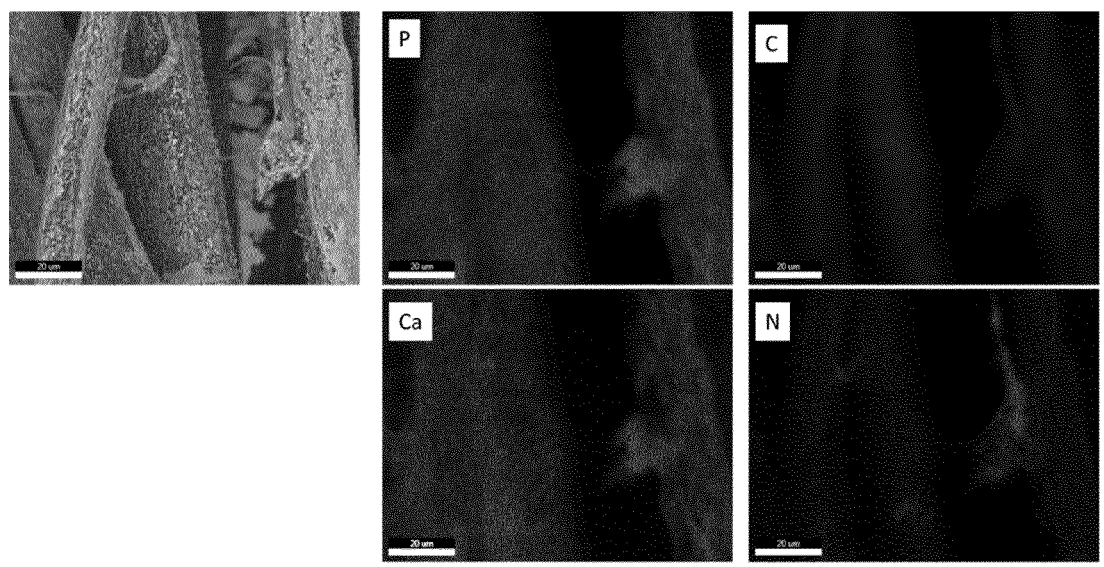
FIG. 12 shows SEM-EDX images for some elements of composite fiber loaded with 15 mass % HA, after plasma etching and culturing with hMSCs for 28 days.

In FIG. 12 elemental mapping using SEM-EDX is also shown as images for the different elements, as obtained for the knitted sample comprising composite fiber loaded with 15 mass % HA, and after plasma etching, and culturing with hMSCs for 28 days.

TABLE 8

| Element | Area 1 | Area 2 | Area 3 |
|---|---|---|---|
| C | 1328.8 | 662.2 | 1028.1 |
| Ca | 30.1 | 143.3 | 89.5 |
| Ca/C ratio | 0.02 | 0.22 | 0.09 |

(Net. Int. means net intensity of the signal)

TABLE 9

| Element | Area 1 (Net Int.) | Area 2 (Net Int.) | Area3 (Net Int.) | Area 4 (Net Int.) |
|---|---|---|---|---|
| C | 1036.0 | 101.9 | 552.8 | 282.1 |
| Ca | 8.2 | — | — | 21.5 |
| (Ca)/C ratio | 0.01 | > | > | 0.08 |

(Net. Int. means net intensity of the signal; — means no measurable result)

The invention claimed is:

1. A high-strength polyolefin composite fiber, which fiber has a fiber body consisting of a composition, optionally a spin finish, and optionally an anti-microbial agent on the surface of the fiber, the composition consisting of:
   a) a polyolefin, wherein the polyolefin is ultra-high molecular weight polyethylene (UHMWPE);
   b) 1-30 mass % of bioceramic particles having particle size D50 of 0.01-10 µm;
   c) at most 0.05 mass % of residual spin solvent;
   d) optionally 0-3 mass % of other additives selected from the group consisting of anti-static agents, anti-oxidants, stabilizers, colorants, lubricants, and combinations thereof; and
   wherein the sum of a)-d) is 100 mass %;
   wherein the fiber body has bioceramic particles exposed at the surface of the fiber body, partly embedded in the surface of the fiber body, and not fully covered by the polyolefin and the bioceramic particles show bioactivity, in addition to bioceramic particles that are fully embedded in the polyolefin and not exposed at the surface of the fiber body, and wherein the fiber has a tensile strength of at least 15 cN/dtex.

2. The high-strength polyolefin composite fiber according to claim 1, wherein the bioceramic particles are calcium phosphates, bioactive glass, or mixtures thereof.

3. The high-strength polyolefin composite fiber according to claim 1, wherein the bioceramic particles are substantially spherical, ellipsoidal or cubical, having an aspect ratio of at most 5.

4. The high-strength polyolefin composite fiber according to claim 1, wherein the bioceramic particles are present in an amount of from 2 to 22 mass % of the composition.

5. The high-strength polyolefin composite fiber according to claim 1, wherein the fiber is a multi-filament yarn with titer of 10 to 2000 dtex and comprises filaments with a diameter of from 5 to 50 µm.

6. The high-strength polyolefin composite fiber according to claim 1, wherein the fiber has a tenacity of at least 20 cN/dtex.

7. The high-strength polyolefin composite fiber according to claim 1, wherein the fiber has a surface coverage by exposed bioceramic particles of 0.1-25 area % as determined with XPS and AFM surface analysis.

8. The high-strength polyolefin composite fiber according to claim 1, wherein the fiber shows at least 25% higher ALP activity after 28 days in an ALP assay compared to a corresponding fiber containing no bioceramic particles.

9. The high-strength polyolefin composite fiber according to claim 1, wherein the bioceramic particles comprise a mixture of hydroxyapatite and tricalcium phosphate in a mass ratio of 90:10 to 10:90.

10. The high-strength polyolefin composite fiber according to claim 1, wherein the bioceramic particles have a particle size of at least 10 nm and of at most 8 μm.

11. A biomedical device or implant comprising a plurality of the composite fiber according to claim 1.

12. The biomedical device or implant according to claim 11, wherein the device or implant is a permanent high-strength orthopedic implant for repairing bone fractures or torn ligaments or tendons.

13. The biomedical device or implant according to claim 11, wherein the device or implant is selected from the group consisting of flexible tissue anchors, cortical fixation devices, high-strength orthopedic sutures, transosseous cerclage cables, synthetic tendons, synthetic ligament grafts, interspinous spacers, spinal disc prostheses, spinal fusion devices, and synthetic scaffolds to repair bone voids.

14. A method for making high-strength UHMWPE composite fibers by a gel-spinning process comprising steps of:
   i. preparing a spin mixture consisting of:
      a) UHMWPE having an intrinsic viscosity of between 5 and 40 dL/g;
      b) bioceramic particles with particle size D50 of 0.01-10 μm when dispersed in decalin;
      c) optionally other additives selected from the group consisting of anti-static agents, anti-oxidants, stabilizers, colorants, lubricants, and combinations thereof; and
      d) a spin solvent;
   ii. spinning the spin mixture through a multiple orifice die plate to form solvent-containing composite fibers;
   iii. drawing the solvent-containing composite fibers in at least one drawing step; and
   iv. removing at least partly the spin solvent from the solvent-containing composite fibers before, during, or after drawing the solvent-containing composite fibers.

15. The method according to claim 14, further comprising the step of post-treating the surface of the fibers.

16. The method according to claim 14, further comprising a step of post-treating the surface of the fibers by plasma etching in an oxygen-containing atmosphere.

17. The high-strength polyolefin composite fiber according to claim 1, wherein the bioceramic particles are present in an amount of from 2 to 10 mass % of the composition.

18. The high-strength polyolefin composite fiber according to claim 1, wherein the bioceramic particles comprise a mixture of hydroxyapatite and bioactive glass in a mass ratio of 90:10 to 10:90.

19. The high-strength polyolefin composite fibers according to claim 1, wherein the fiber body is formed by a gel-spinning process comprising steps of:
   i. preparing a spin mixture consisting of:
      a) UHMWPE having an intrinsic viscosity of between 5 and 40 dL/g;
      b) bioceramic particles with particle size D50 of 0.01-10 μm when dispersed in decalin;
      c) optionally other additives selected from the group consisting of anti-static agents, anti-oxidants, stabilizers, colorants, lubricants, and combinations thereof; and
      d) a spin solvent;
   ii. spinning the spin mixture through a multiple orifice die plate to form solvent-containing composite fibers;
   iii. drawing the solvent-containing composite fibers in at least one drawing step; and
   iv. removing at least partly the spin solvent from the solvent-containing composite fibers before, during, or after drawing the solvent-containing composite fibers.

* * * * *